US011103523B2

United States Patent
Lu et al.

(10) Patent No.: US 11,103,523 B2
(45) Date of Patent: Aug. 31, 2021

(54) SELF-ASSEMBLED BRUSH BLOCK COPOLYMER-NANOPARTICLES FOR DRUG DELIVERY

(71) Applicant: UNIVERSITY OF CONNECTICUT, Farmington, CT (US)

(72) Inventors: Xiuling Lu, Storrs, CT (US); Rajeswari Kasi, Bala Cynwyd, PA (US); Thanh-Huyen Tran, Willington, CT (US); Chi Thanh Nguyen, Willington, CT (US); Prashant Deshmukh, Willington, CT (US)

(73) Assignee: University of Connecticut, Farmington, CT (US)

( * ) Notice: Subject to any disclaimer, the term of this patent is extended or adjusted under 35 U.S.C. 154(b) by 502 days.

(21) Appl. No.: 15/027,791

(22) PCT Filed: Oct. 7, 2014

(86) PCT No.: PCT/US2014/059517
§ 371 (c)(1),
(2) Date: Apr. 7, 2016

(87) PCT Pub. No.: WO2015/054269
PCT Pub. Date: Apr. 16, 2015

(65) Prior Publication Data
US 2016/0243141 A1 Aug. 25, 2016

Related U.S. Application Data

(60) Provisional application No. 61/887,781, filed on Oct. 7, 2013.

(51) Int. Cl.
*A61K 31/704* (2006.01)
*A61K 9/52* (2006.01)
(Continued)

(52) U.S. Cl.
CPC .......... *A61K 31/704* (2013.01); *A61K 9/5115* (2013.01); *A61K 9/5138* (2013.01);
(Continued)

(58) Field of Classification Search
CPC .............. A61K 31/704; A61K 31/7042; A61K 31/7046; A61K 47/28; A61K 47/34; C08F 293/00
See application file for complete search history.

(56) References Cited

U.S. PATENT DOCUMENTS

| 4,971,803 A * | 11/1990 | Li ........................ A61K 9/1272 264/4.1 |
| 2009/0209508 A1* | 8/2009 | Lange ...................... B82Y 5/00 514/185 |
| 2018/0207184 A1* | 7/2018 | Kasi ....................... A61K 45/06 |

FOREIGN PATENT DOCUMENTS

| JP | 2012-194533 | 10/2012 |
| WO | 2001/91725 A2 | 12/2001 |

(Continued)

OTHER PUBLICATIONS

Zhang et al. Amphiphilic liquid-crystal block copolymer nanofibers via RAFT-mediated dispersion polymerization. Soft Matter, 2012, 8, 1130-1142.*
(Continued)

*Primary Examiner* — Lakshmi S Channavajjala
(74) *Attorney, Agent, or Firm* — McDonnell Boehnen Hulbert & Berghoff LLP

(57) ABSTRACT

The invention provides amphiphilic liquid crystalline brush block copolymers that can readily self-assemble to nanoparticles in aqueous solutions and also allow for encapsulation of hydrophobic pharmaceutically active molecules.

26 Claims, 14 Drawing Sheets

(51) Int. Cl.
*C08F 293/00* (2006.01)
*A61K 9/51* (2006.01)
*C08F 220/28* (2006.01)

(52) U.S. Cl.
CPC .......... *A61K 9/5146* (2013.01); *A61K 9/5192* (2013.01); *C08F 293/005* (2013.01); *C08F 220/281* (2020.02); *C08F 220/286* (2020.02); *C08F 2438/03* (2013.01)

(56) References Cited

FOREIGN PATENT DOCUMENTS

WO   2009/022477   11/2010
WO   2009/113645   7/2011

OTHER PUBLICATIONS

Zhou et al. Hierarchically Structured Free-Standing Hydrogels with Liquid Crystalline Domains and Magnetic Nanoparticles as Dual Physical Cross-Linkers. J. Amer. Chem. Soc. 2012. 134, 1630-1641.*

Zhou et al. Polymers Comprising Cholesterol: Synthesis, Self-Assembly, and Applications. Materials. 2: 636-660 (Year: 2009).*

International Search Report for PCT/US2014/059517, dated Mar. 30, 2015.

Bagheri, et al., "Self-assembled micellar nanoparticles of a novel amphiphilic cholesteryl-poly(l-lactic acid)-b-poly (poly(ethylene glycol)methacrylate) block-brush copolymer," Iranian Polymer Journal, 22(4): 293-302, Jan. 2013.

Prashant, et al., "hierarchically self-assembled photonic materials from liquid crystalline random brush copolymers," Macromolecules, 46(11): 4558-4566, Jun. 2013.

Nguyen, et al. "Self-assembled nanoparticles from thiol functionalized liquid crystalline brush block copolymers for dual encapsulation of doxorubicin and gold nanoparticles," Polymer Chemistry 2014, 5 (8), 2774-2783.

Yu Shao, et al., Multishape Memory Effect of Norbornene-Based Copolymers with Cholic Acid Pendant Groups, Macromolecules, 2012, 45, 1924-1930.

Deshmukh et al. "Interplay between Liquid Crystalline Order and Microphase Segregation on the Self-Assembly of Side-Chain Liquid Crystalline Brush Block Copolymers,"Macromolecules 46(20):8245-8252 (2013).

Xie, Tao. "Tunable polymer multi-shape memory effect," Nature 464:267-270 (2010).

* cited by examiner

SELF-ASSEMBLED BRUSH BLOCK COPOLYMER-NANOPARTICLES FOR DRUG DELIVERY

CROSS-REFERENCE TO RELATED APPLICATION

This application is a U.S. national phase of International Application No. PCT/US2014/059517, filed on Oct. 7, 2014, which claims priority to U.S. Provisional Application No. 61/887,781, filed Oct. 7, 2013, both of which are incorporated by reference herein in their entirety.

BACKGROUND OF THE INVENTION

Field of the Invention

The invention provides amphiphilic liquid crystalline brush block copolymers that can readily self-assemble to nanoparticles in aqueous solutions and also allow for encapsulation of hydrophobic pharmaceutically active molecules.

Description of the Related Art

Clinical use of anticancer drugs is limited due to its hydrophobicity and non-specific toxicity because the majority of clinically used anticancer drugs are low molecular compounds that diffuse rapidly though the body in both healthy and diseased tissue causing serious side effects. There is a growing need to develop safe and effective delivery systems for anticancer drugs. Self-assembled nanoparticle structures allow encapsulation of the anticancer drugs in the core while the hydrophilic shell allows for increased water solubility and stability. Nanoparticles with appropriate size and surface property may have opportunity to accumulate in tumor sites through the enhanced permeability and retention (EPR) effect, which results from abnormalities of tumor blood and lymphatic vasculature.

Various self-assembled nanoparticles have been developed for delivery of anticancer drugs. Unfortunately, most of these have not shown beneficial effects in clinical trials. The major obstacle for drug-delivery polymer systems is the lack of stability of polymer micelles at high dilution and low drug loading levels. Furthermore, many synthetic biodegradable copolymers upon erosion in vivo yield oligomers and monomers that adversely interact with the surrounding tissue.

Copolymers with cholesterol end-groups have also generated interest for various biomedical applications including serving as membranes for cell attachment and proliferation, forming the basis of polymeric scaffolds, and as materials with improved blood compatibility. But, reported amphiphilic polymer architectures that contain cholesterol are conjugates or linear copolymers with only one or a few cholesterol molecules. This results in low stability, limited drug loading capacity to 20% (w/w) with low encapsulation efficiency and fast drug release for these cholesterol-containing copolymers.

SUMMARY OF THE INVENTION

Designing block copolymers with appropriate architecture and composition to increase drug loading capacity, but at the same time minimize the toxicity of the polymer carrier and its degradation products, still presents a challenge. Liquid crystalline polymers (LCPs) comprising cholesterol molecules have been applied in various fields such as bioactive materials and biotechnology, but only few researchers utilized LCPs for drug delivery systems. The present invention provides novel liquid crystalline brush block copolymers ("LCbrushBCP" or "block copolymers"). The block copolymers of the disclosure readily formed self-assembled nanoparticles in aqueous solutions. These nanoparticles allowed for loading of hydrophobic drugs simply via self-assembly without sonication or homogenization procedure. The nanoparticles of the disclosure also showed excellent stability of the high steroid content hydrophobic core and demonstrated a high capacity for encapsulation of hydrophobic drugs, while the brush-like hydrophilic molecules on the surface allowed for stability of the nanoparticles in aqueous medium. The hydrophilic surface also protected from reticuloendo-thelial system (RES) uptake and facilitated long circulation in body. The self-assembled nanoparticles of the disclosure have good biocompatibility, high drug loading capacity, long retention in the circulation, multimodality potential, and can be easily manufactured in large scale, which make them suitable for drug delivery.

The nanostructures of the disclosure that encapsulated a hydrophobic anticancer drug showed high tumor accumulation and antitumor efficacy with significantly reduced toxicity compared to the free anticancer drug. These properties make the nanoparticles of the disclosure especially suitable for use in anti-cancer drug delivery.

Finally, the block copolymers of the disclosure may be functionalized (for example, with thiol, phosphate, carboxylic acid groups, etc.), and such copolymers also self-assembled in aqueous media to form well-defined nanoparticles. For example, the thiol functionalized nanoparticles served as a multifunctional carrier for dual encapsulation of hydrophobic anticancer drug via physical entrapment and gold nanoparticles (Au NPs) via covalent bonding to the thiol groups. High drug loading and high encapsulation efficiency, along with uniform size distribution and good stability, allow the functionalized nanoparticles to be used for the delivery of anticancer drug and metal nanoparticles, for example in photothermal cancer therapy and biological sensing.

Thus, in a broad aspect, the disclosure provides a block copolymer comprising: a first block, which is of formula:

and a second block, which is of formula:

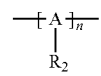

wherein m and n are independently an integer about 3 to about 500;

A is independently selected from polynorbonene, polycyclopentene, polycyclooctene, polyacrylate, polymethacrylate, and a polysiloxane;

$R_1$ is a steroid moiety optionally comprising a linker; and $R_2$ is polyalkylene oxide moiety.

In another aspect, the disclosure provides the block copolymers of the disclosure in a core/shell nanoparticle form. In one embodiment, the core/shell nanoparticle form is wherein the block copolymers of the disclosure self-assembled in aqueous solutions.

In one aspect, the disclosure provides a nanoparticle comprising the block copolymer of the disclosure and a hydrophobic pharmaceutically active molecule. Another aspect provides a therapeutic delivery system comprising this nanoparticle. Yet another aspect provides a method of delivering a pharmaceutically active molecule, comprising administering to a subject this nanoparticle. Yet another aspect provides a method of treating a disease or disorder, comprising administering to a subject this nanoparticle. For example, if the hydrophobic pharmaceutically active molecule is an anti-cancer drug, then the disease or disorder is cancer.

Finally, the disclosure also provides a process for preparing a nanoparticle of the disclosure: comprising (a) dissolving a block copolymer of the disclosure in an organic solvent to obtain a copolymer solution; and (b) mixing the copolymer solution in an aqueous solution to form the nanoparticle.

BRIEF DESCRIPTION OF THE DRAWINGS

FIG. 1 illustrates self-assembly in aqueous media of dual Au NP and DOX-encapsulated P(PEOA$_{SH}$-b-C5A), while

DETAILED DESCRIPTION OF THE INVENTION

Figure 1:
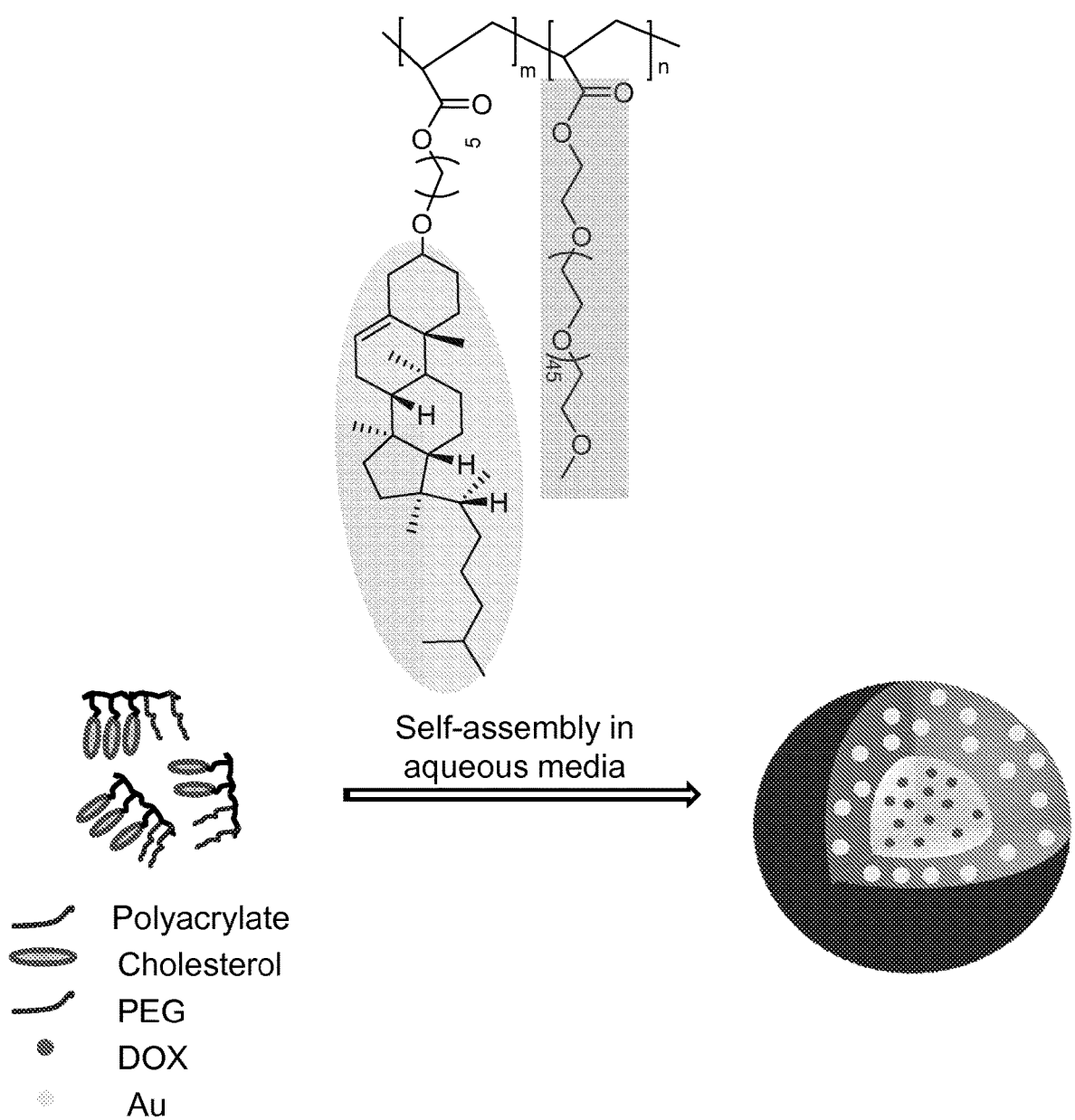
Figure 2:
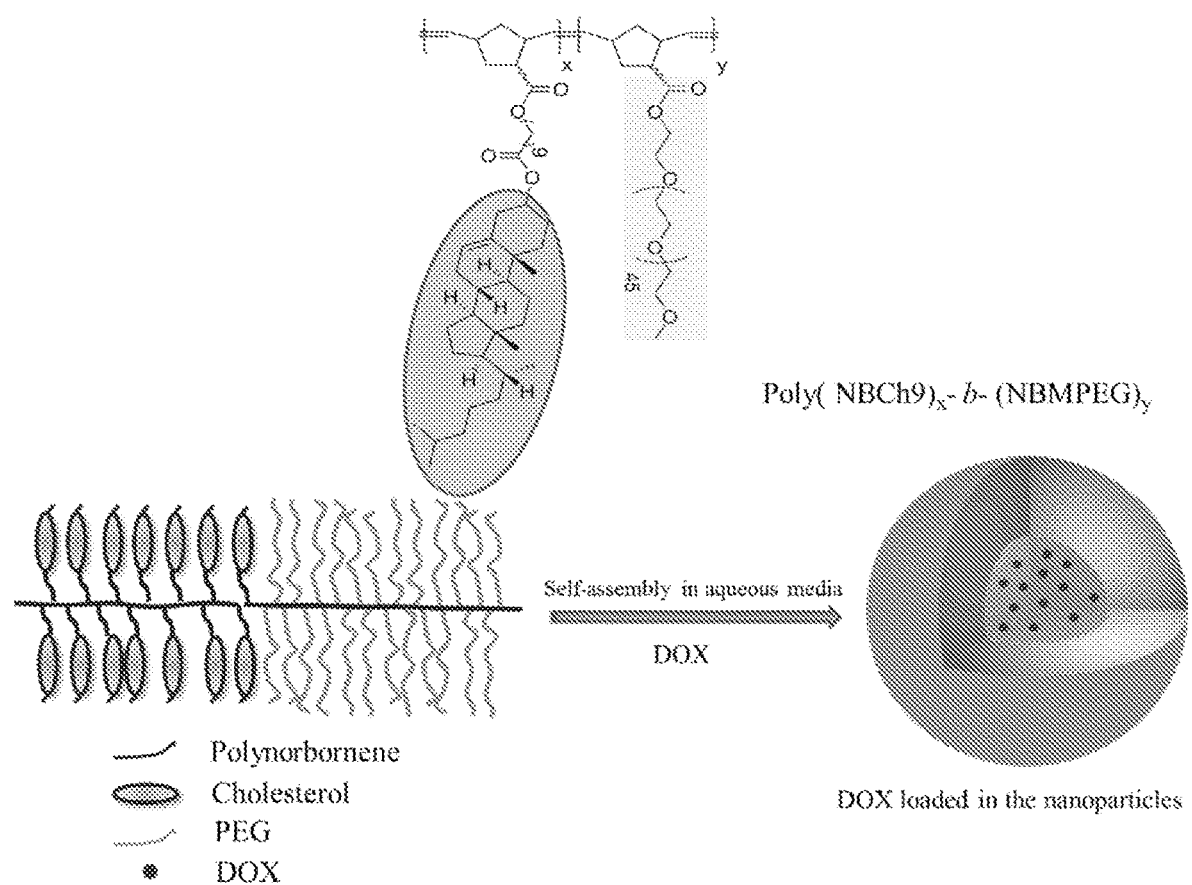
FIG. 2 illustrates self-assembly of P(NBCh9-b-NBPEG) copolymers in aqueous media.

Before the disclosed methods and materials are described, it is to be understood that the aspects described herein are not limited to specific embodiments, methods, apparati, or configurations, and as such can, of course, vary. It is also to be understood that the terminology used herein is for the purpose of describing particular aspects only and, unless specifically defined herein, is not intended to be limiting.

In view of the present disclosure, the methods described herein can be configured by the person of ordinary skill in the art to meet the desired need. For example, in certain aspects, the copolymers of disclosure comprise of a steroid-containing block and a polyalkylene oxide-containing block. Such copolymers readily self-assemble as nanoparticles in aqueous solutions without sonication or homogenization, and have good biocompatibility, high drug loading capacity, long retention in the circulation, multimodality potential and can be easily manufactured in large scale. In another example, the nanostructures of the disclosure may be used to encapsulate a hydrophobic therapeutically active molecule, such as anti-cancer drugs. The nanoparticles encapsulating anticancer drug showed high tumor accumulation and antitumor efficacy with significantly reduced toxicity compared to the free anticancer drug. In another example, the block copolymers of the disclosure may be functionalized (for example, with thiol), and such copolymers also self-assembled in aqueous media to form well-defined nanoparticles with the functional group. The thiol functionalized nanoparticles served as a multifunctional carrier for dual encapsulation of hydrophobic anticancer drug via physical entrapment and gold nanoparticles (Au NPs) via covalent bonding to the thiol groups. These dual nanoparticles exhibited high drug loading, high encapsulation efficiency, uniform size distribution, and good stability.

The block copolymers of the disclosure require that the first block comprises a steroid moiety optionally comprising a linker. As the person of ordinary skill in the art will appreciate, suitable steroids may be selected to meet the desired need. For example, the steroid moiety suitable in the materials of the disclosure comprises cholesterol, cholic acid, deoxycholic acid, taurocholic acid or the like. In one embodiment, the steroid moiety comprises cholesterol.

The steroid moiety may be connected to the polymer backbone via a suitable linker. Some examples of linkers include, but are not limited to:

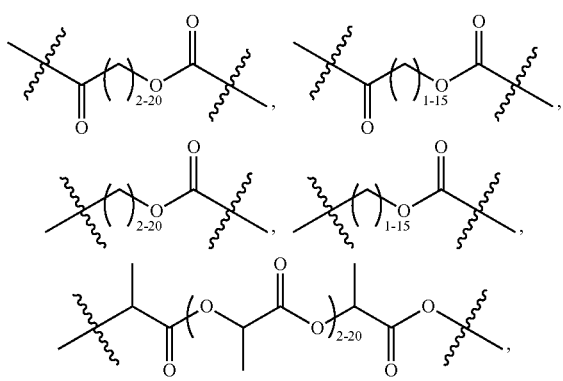

a polylactone, or an oligomer of siloxane. In one embodiment, the linker at $R_1$ is:

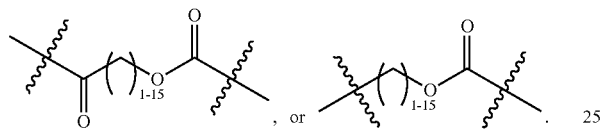

In another embodiment, the linker at $R_1$ is:

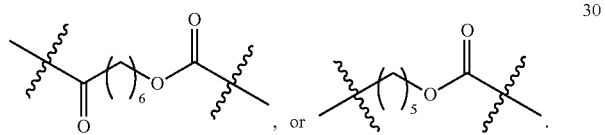

The steroid-containing first block may be present from about 1% to about 80% of the total weight of the block copolymer (i.e., weight fraction of about 1% to about 80%.) For example, the weight fraction of the first block may be more that 50%, or less than 50%, or from about 5% to about 70%, or about 40% to about 70%, or about 40% to about 50%, or about 60% to about 70%, or about 2% to about 30%, or about 3% to about 30%, or about 5% to about 30%, or about 2% to about 20%, or about 3% to about 20%, or about 5% to about 20%, or about 7% to about 20%, based on the total weight of the block copolymer.

The block copolymers of the disclosure require that the second block comprises a polyalkylene oxide moiety. As the person of ordinary skill in the art will appreciate, suitable polyalkylene oxides may be selected to meet the desired need. In some embodiments, the polyalkylene oxide moiety comprises polyethylene oxide or polyethylene oxide thiolate. In another embodiment, the polyalkylene oxide moiety comprises polyethylene oxide.

The polyalkylene oxide-containing second block may be present from about 20% to about 99% of the total weight of the block copolymer (i.e., weight fraction of about 20% to about 99%.) For example, the weight fraction of the second block may be more that 50%, or less than 50%, or from about 30% to about 95%, or about 30% to about 60%, or about 50% to about 60%, or about 30% to about 40%, or about 70% to about 98%, or about 70% to about 97%, or about 70% to about 95%, or about 80% to about 98%, or about 8% to about 97%, or about 80% to about 95%, or about 80% to about 93%, based on the total weight of the block copolymer.

The block copolymers of the disclosure require a backbone moiety A. The block copolymers described herein may contain, for example, polynorbonene, polycyclopentene, polycyclooctene, polyacrylate, polymethacrylate, and a polysiloxane backbone A available to one skill in the art, and may be varied depending on the desired product. In one embodiment, the block copolymers of disclosure are those wherein each A is independently polynorbonene or polyacrylate. In another embodiment, each A is independently polynorbonene. In another embodiment, each A is independently polyacrylate.

In one embodiment, the block copolymers of the disclosure comprise the structure:

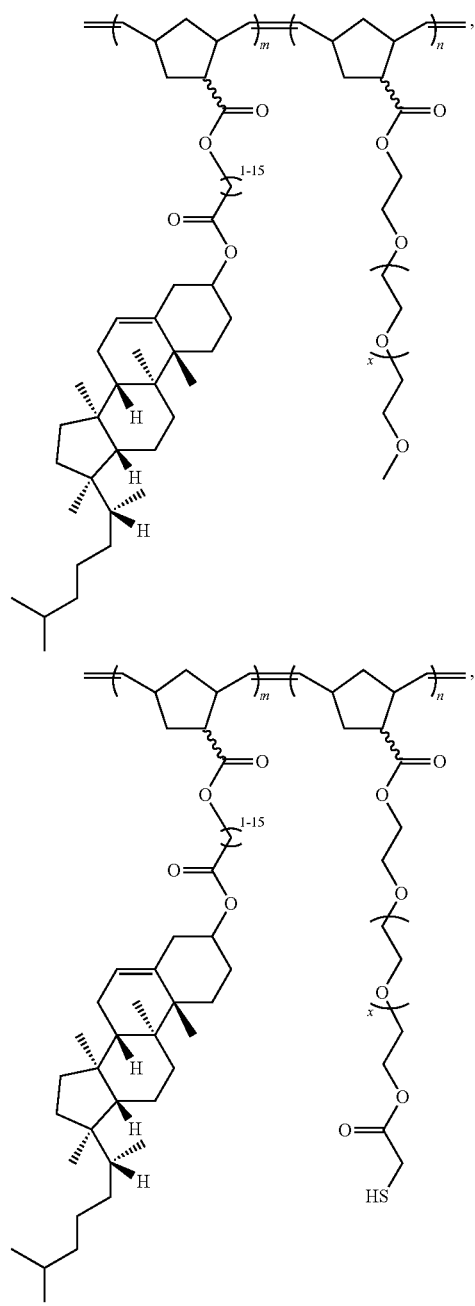

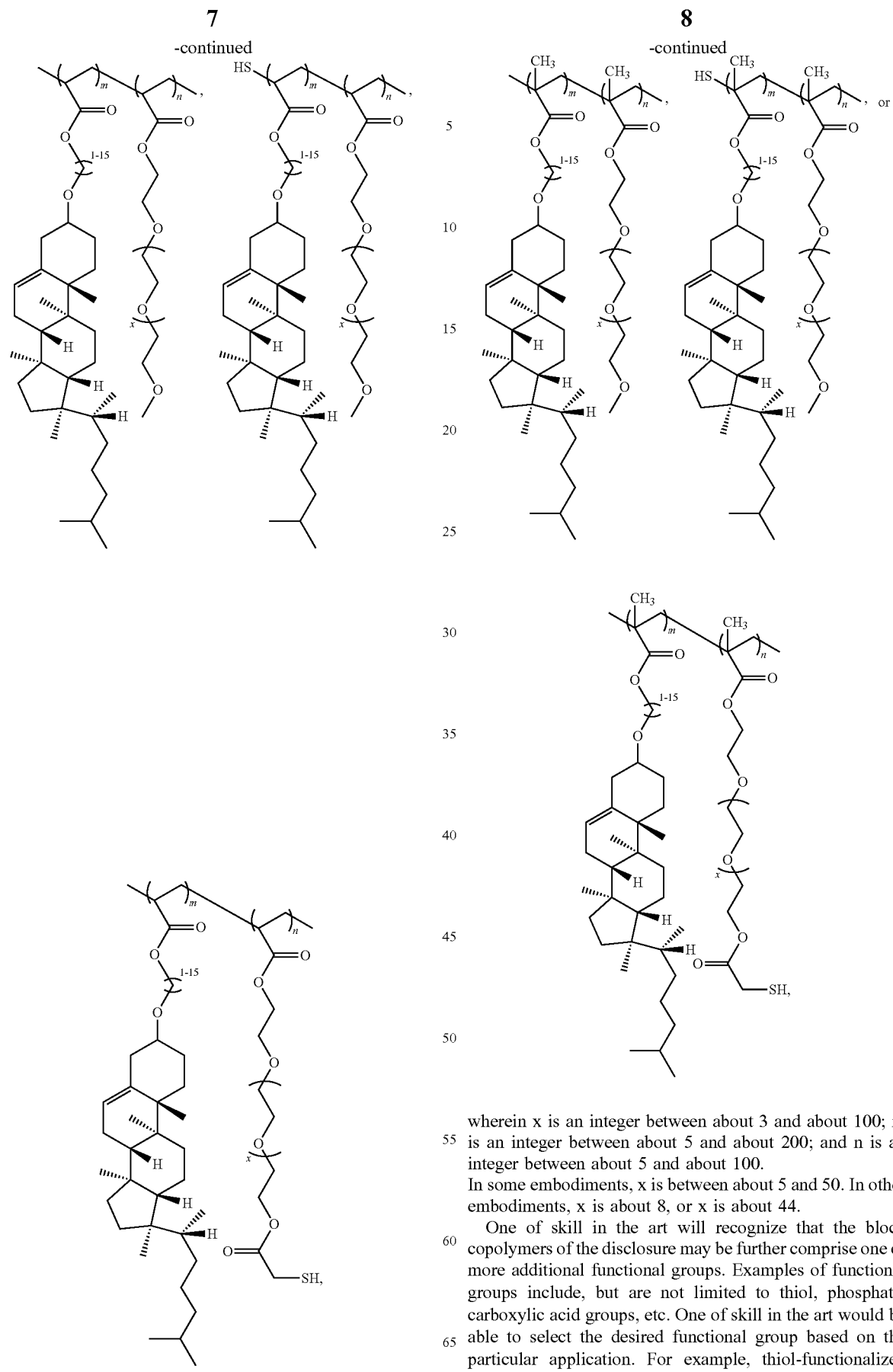

wherein x is an integer between about 3 and about 100; m is an integer between about 5 and about 200; and n is an integer between about 5 and about 100.

In some embodiments, x is between about 5 and 50. In other embodiments, x is about 8, or x is about 44.

One of skill in the art will recognize that the block copolymers of the disclosure may be further comprise one or more additional functional groups. Examples of functional groups include, but are not limited to thiol, phosphate, carboxylic acid groups, etc. One of skill in the art would be able to select the desired functional group based on the particular application. For example, thiol-functionalized block copolymer may serve as a multifunctional carrier for dual encapsulation of hydrophobic anticancer drug (i.e., via physical entrapment) and gold nanoparticles (Au NPs) via covalent bonding to the thiol groups. Likewise, phosphate- or carboxylic acid-functionalized block copolymer may be used to encapsulate the quantum dots (e.g., CdSe or the like) or magnetic nanoparticles.

The values of m and n may be selected by one of skill in the art and may be varied depending on the desired product. For example, m may be between about 10 and about 100; and/or n may be between about 15 and about 85. The molecular weight of the block copolymer of the disclosure may be between about 10,000 and about 1,000,000 Da. In one embodiment, the block copolymer of the disclosure is about 40,000 to about 750,000 Da, or about 60,000 to about 700,000 Da, or about 60,000 to about 100,000 Da, or about 40,000 to about 200,000 Da.

The block copolymers disclosed herein have a number of desirable qualities including for example, a relatively low polydispersity. Optionally in embodiments of the invention, the polymer chains exhibit a polydispersity index such that $M_w/M_n$ is between about 1.0 and about 2.5. In some embodiments, the polydispersity index is between about 1.0 and about 2.0, or between about 1.0 and about 1.9, or between about 1.1 and about 1.9, or between about 1.0 and about 1.8, or between about 1.1 and about 1.8, or between about 1.0 and about 1.5, or between about 1.5 and about 1.5, or between about 1.0 and about 1.3, or between about 1.0 and about 1.2, or about 1.0, or about 1.1, or about 1.2, or about 1.3, or about 1.4, or about 1.5, or about 1.6, or about 1.7, or about 1.8, or about 1.9, or even about 2.0. In certain embodiments, the polymer exhibits a polydispersity of $M_n/M_w$ between about 1.0 and about 1.5. In some other embodiments, the polymer exhibits a polydispersity of $M_w/M_n$ between about 1.0 and about 1.2.

In another aspect, the disclosure provides the block copolymers of the disclosure in a core/shell nanoparticle form. In one embodiment, the core/shell nanoparticle form is wherein the block copolymers of the disclosure self-assembled in aqueous solutions. In one aspect, the disclosure provides a nanoparticle comprising the block copolymer of the disclosure and a hydrophobic pharmaceutically active molecule. Any suitable hydrophobic pharmaceutically active molecule may be used depending on the desired therapeutic effect. Some examples include, but are not limited to doxorubicin, daunorubicin, vincristin, paclitaxel, docetaxel, cisplatin, camptothecin, irinotecan, 5-fluorouracil, methotrexate, or dexamethasone.

The nanoparticles of the disclosure may further comprise one or more of metal nanoparticles, such as gold nanoparticles and/or magnetic nanoparticles and/or quantum dots (for example, CdSe and the like).

The block copolymers disclosed herein have a number of desirable qualities including for example, well-defined with uniform size distribution. The nanoparticles of the disclosure may be anywhere from about 5 to about 500 nm in size. For example, the nanoparticles may be between about 10 and about 200 nm, or between about 50 and about 150 nm, or between about 100 and about 250 nm, or between about 100 and about 200 nm, or between about 120 and about 150 nm, or between about 110 and about 150 nm, or between about 120 and about 180 nm, or between about 150 and about 250 nm, or between about 150 and about 200 nm.

Definitions

Throughout this specification, unless the context requires otherwise, the word "comprise" and "include" and varia- tions (e.g., "comprises," "comprising," "includes," "includ- ing") will be understood to imply the inclusion of a stated component, feature, element, or step or group of compo- nents, features, elements or steps but not the exclusion of any other integer or step or group of integers or steps.

As used in the specification and the appended claims, the singular forms "a," "an" and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approxima- tions, by use of the antecedent "about," it will be understood that the particular value forms another aspect. It will be further understood that the endpoints of each of the ranges are significant both in relation to the other endpoint, and independently of the other endpoint.

As used herein the term "combining" includes adding one or more items to a reaction mixture.

As used herein the term "dispersity," "polydispersity," "polydispersity index", "PDI," and "$M_w/M_n$," are used inter- changeably and refer to measure of the polymer uniformity with respect to distribution of molecular mass. The disper- sity may be calculated by dividing weight average molecular weight ($M_w$) by the number average molecular weight ($M_n$) (i.e., $M_w/M_n$). In certain embodiments, the dispersity may be calculated according to degree of polymerization, where the dispersity equals $X_w/X_n$, where $X_w$ is the weight-average degree of polymerization and $X_n$ is the number-average degree of polymerization.

All percentages, ratios and proportions herein are by weight, unless otherwise specified. A weight percent (weight %, also as wt %) of a component, unless specifically stated to the contrary, is based on the total weight of the compo- sition in which the component is included (e.g., on the total amount of the reaction mixture).

EXAMPLES

The materials and methods of the disclosure are illustrated further by the following examples, which are not to be construed as limiting the disclosure in scope or spirit to the specific procedures and materials described in them.

Materials and Methods

All glassware was stored in a drying oven for several hours at 120° C. Doxorubicin hydrochloride (DOX.HCl) and idarubicin hydrocholoride were purchased from BiotangInc (Waltham, Mass., USA). Pyrene was obtained from the Sigma-Aldrich Chemical Co. (St. Louis, Mo., USA). Triethylamine (TEA) and dimethyl formamide (DMF) were purchased from Fisher Scientific (Boston, Mass., USA). Penicillin-streptomycin, 0.25% (w/v) trypsine-0.03% (w/v) EDTA solution, RPMI 1640, and DMEM medium were purchased from American Type Cul- ture Collection (Rockville, Md., USA). Human cervical cancer cells (Hela) and human lung cancer cell lines (A549) were purchased from the National Cancer Institute (Freder- ick, Md., USA). Fetal bovine serum (FBS) was purchased from Atlanta Biologicals (Norcross, Ga., USA). Draq5, 1,1'-Dioctadecyl-3,3,3',3'-tetramethylindotricarbocyanine iodide (DiR) and in vitro toxicology assay kits (MTT based) were obtained from Invitrogen (Carlsbad, Calif., USA).

Spectra/Pro membranes were purchased from Spectrum Laboratories, Inc. (Rancho Dominguez, Calif., USA). The 2,2'-azo-bis(isobutyronitrile) (AIBN), thioglycolic acid (98%), p-toluene sulfonic acid monohydrate (PTSA), D,L-dithiothreitol (DTT), chloroauric acid (HAuCl4.3H2O), sodium citrate, cholesterol (96%), 1,5-pentanediol (>97%) were obtained from Aldrich, USA. Triethylamine (TEA) and dimethyl formamide (DMF) were purchased from Fisher Scientific (Boston, Mass., USA). Polyethylene glycol (MW=1500), 1,4-dioxane (99.8%, extra dry), dichloromethane (DCM) (99.9%, extra dry), acryloyl chloride (>97%) were purchased from Acros Organics USA. 5-cholesteryloxypentyl acrylate (C5A), was prepared according to published procedures. The RAFT agent S-1-dodecyl-S'-(α,α'-dimethyl-α"-acetic acid) tricarbonate (CTA) was synthesized according to a published procedure. Tween® 80 (polysorbate 80) was received as a gift from Croda (Columbus Circle Edison, N.J.). All chemicals were analytical grade and used without purification.

Data is expressed as mean±standard deviation. The statistical significance of difference between experimental and control groups was determined using a student's t-test. A probability (p) of less than 0.05 was considered statistically significant.

Example 1

Synthesis and Purification of P(PEOA$_{SH}$-b-C5A)

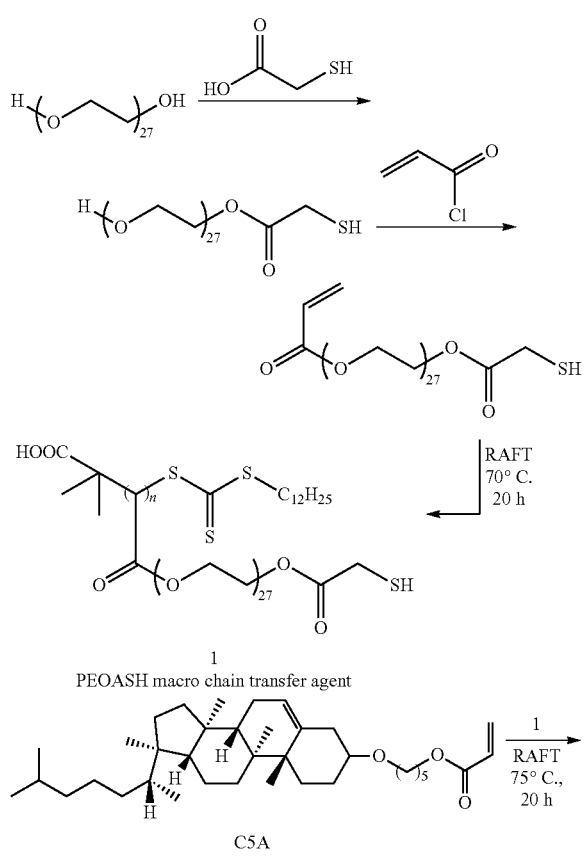

Scheme 1

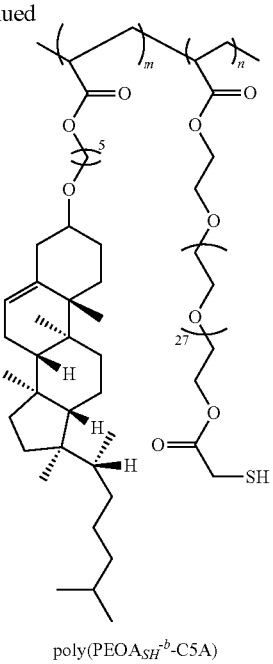

poly(PEOA$_{SH}$$^b$-C5A)

All block copolymers were synthesized using controlled radical polymerization such as reversible addition fragmentation transfer (RAFT) as described in C. T. Nguyen, et al. (*Polymer Chemistry* 2014, 5 (8), 2774-2783). Briefly, polyethylene glycol (MW=1500 Da) (1 mmol) and PTSA (0.1 mmol) were added into a round bottom flask and toluene (10 ml) was added. To this reaction mixture, thioglycolic acid (0.5 mmol) was added slowly and this mixture was refluxed overnight under nitrogen atmosphere. After cooling down the reaction mixture, the solvent was removed by evaporation and the residue was partitioned using DCM/water, dried over magnesium sulfate. The organic layer was collected and concentrated under low pressure. To reduce the disulfide functional group, the collected compound was dissolved in methanol followed by adding DTT (1 mmol) and stirred for 3 h at room temperature. The resulting solution was then precipitated in diethyl ether to remove DTT and the thiolated PEO (PEO$_{SH}$) product was obtained as white solid. $^1$H NMR (CDCl$_3$, δ ppm): 4.27 (t, 2H, —COOCH$_2$—, in PEO end group), 3.79-3.44 (m, —CH$_2$CH$_2$O—, repeating units of PEO), 3.35 (s, 2H), 1.55 (s, —SH), $^{13}$C NMR (CDCl$_3$, δ ppm): 170.9 (—COO), 70.3 and 64.8 (—CH$_2$ in repeat unit of PEO), 27.7 (—CH$_2$—S).

First, PEO$_{SH}$ was dissolved in DCM at the concentration of 10 wt %. Next, acryloyl chloride and TEA were added into the solution and stirred overnight under nitrogen atmosphere. The molar ratio of PEO$_{SH}$, acryloyl chloride and TEA was 1:2:2. After the reaction was completed, the insoluble salt (TEA.HCl) was filtered out, and the solution was collected. Polyethylene oxide thiolate acrylate (PEOA$_{SH}$) was precipitated in excess cold diethyl ether and collected as light yellow solid. $^1$H NMR (CDCl$_3$, δ ppm): 4.27 (t, 2H, —COOCH$_2$—, in PEO end group), 3.79-3.44 (m, —CH$_2$CH$_2$O—, repeating units of PEO), 6.42, 6.09, 5.54 (m, 3H, CH$_2$—CH=COO—). $^{13}$C NMR (CDCl$_3$, δ ppm): 170.9 (—COO), 133, 126.6 (—CH$_2$, CH in vinyl group), 70.3 and 64.8 (—CH$_2$ repeat unit in PEO), 27.7 (—CH$_2$—S).

The P(PEOA$_{SH}$) macro chain transfer agent was synthesized using RAFT polymerization. Monomer PEOA$_{SH}$ (0.5 g, 0.93 mmol) was dissolved in 3 mL of toluene in a Schlenk tube equipped with a stir bar, followed by the addition of the RAFT agent CTA (18.3 mg, 0.05 mmol), and the initiator, AIBN (0.82 mg, 0.005 mmol). The Schlenk tube was degassed by three freeze-evacuate-thaw cycles and then placed in a 70° C. oil bath. The reaction was allowed to proceed for 20 h. The reaction mixture was concentrated and precipitated in diethyl ether. The polyacrylate bearing PEO$_{SH}$ (P(PEOA$_{SH}$))polymer was collected and dried in vacuum overnight. $^1$H NMR (CDCl$_3$, δ ppm): 4.27 (t, 2H, —COOCH$_2$—, in PEO end group), 3.79-3.44 (m, —CH$_2$CH$_2$O—, repeating units of PEO), 3.15 (t, 2H, CH$_3$C$_{10}$H$_{20}$CH$_2$—S—), 1.60-1.75 (m, 6H, —S—C(CH$_3$)$_2$COO—), 1.25 (m, 20H, CH$_3$O$_{10}$H$_{20}$CH$_2$S—), 0.87 (t, 3H, CH$_3$O$_{10}$H$_{20}$CH$_2$S—). GPC (40° C., THF mobile phase, polystyrene standards): M$_n$=8540 g/mol, PDI=1.18.

In a representative procedure, a mixture of the P(PEOA$_{SH}$) macro chain transfer agent (1.2 g, 0.2 mmol), C5A (3.8 g, 28.0 mmol), and AIBN (6 mg, 0.04 mmol) were dissolved in 1,4-dioxane (3 mL) and degassed by performing three freeze-evacuate-thaw cycles. The reaction mixture was sealed and then placed in a pre-heated oil bath at 75° C. for 20 h. The resultant mixture was concentrated and precipitated in diethyl ether. The product was collected and dried in vacuum. $^1$H NMR (CDCl$_3$, δ ppm): 5.33 (d, 1H, —C=CH—, olefin group in cholesteryl moiety), 3.9 (m, 2H, —COOCH$_2$CH$_2$), 3.64 (m, —CH$_2$CH$_2$O— repeating units of PEO), 3.45 (m, 2H, —CH$_2$OCH—), 3.12 (m, 1H, —CH$_2$OCH—), 2.50-0.55 (m, 54H, —CH$_3$, —CH$_2$—, —CH—, —CH—(OH$_3$)— in cholesteryl, —CH$_2$—O(CH$_3$)COO—, —CH$_2$CH$_2$—CH$_2$CH$_2$CH$_2$— in spacer). GPC (40° C., THF mobile phase, polystyrene standards): M$_n$=15 270 g/mol, PDI=1.21.

The $^1$H-NMR allowed the determination of molar composition (n: m) and molecular weight of the obtained LCPs block copolymer. The signals at 5.3, 3.9 and 2.5-0.55 ppm were attributed to the protons of cholesterol. Additionally, monomer olefin peaks at 6.42, 6.09 and 5.54 ppm were absent in brush-chol-BCPs, indicative of complete conversion of monomer to polymer. The signals of the PEO block corresponding to PEO repeating unit and CH$_2$ of PEO end group were observed at 3.6 ppm and 4.25 ppm, respectively. By comparing the integration of peaks by $^1$H-NMR spectra at 5.33 ppm (olefin group in cholesteryl moiety) and 3.64 ppm (PEO repeating unit), the weight fraction of the two different blocks were determined. Gel permeation chromatography (GPC) was used to measure the number average molecular (M$_n$) and the polydispersity indices (PDI) of brush-chol-BCPs. The brush-chol-BCPs sharply shifted to a higher molecular weight region with a narrow molecular weight distribution. The results show a monomodal symmetric distribution, indicating a well-controlled polymerization process. Two different brush-chol-BCPs with different weight fractions (or MW) of the cholesterol block were achieved using fixed molecular weight of P(PEOA$_{SH}$) macro chain transfer agents at 9000 g mol$^{-1}$ while the molecular weight of PC5A block was controlled from 7000 to 18000 gmol$^{-1}$ by tuning cholesterol ratio (Table 1).

TABLE 1

Molecular characterization of as-synthesized brush-chol-BCPs polymers

| Polymer | M$_n$ (g/mol) | | Weight fraction[b] (%) | |
| --- | --- | --- | --- | --- |
| | GPC[a] | PDI[a] | PEOA$_{SH}$ | C5A |
| PEO-SH | 1300 | 2.01 | — | — |
| PEOA$_{SH}$ | 2230 | 1.12 | — | — |
| PEOA$_{SH}$ macroinitiators | 8540 | 1.18 | 100 | — |
| P(PEOA$_{SH}$-b-C5A$_{13}$) | 15 270 | 1.21 | 55 | 45 |
| P(PEOA$_{SH}$-b-C5A$_{36}$) | 26 730 | 1.15 | 32 | 68 |

[a]Determined by GPC calibrated at 40° C. with THF as the mobile phase with polystyrene standards.
[b]The ratio of the integrals of peaks by $^1$H-NMR spectra at 5.33 ppm (olefin group in cholesteryl moiety) and 3.64 ppm (PEO repeating unit) is used to calculate the weight fraction of the brush-chol-BCPs.

Example 2

Synthesis and Purification of P(PEO-b-C5MA)-SH

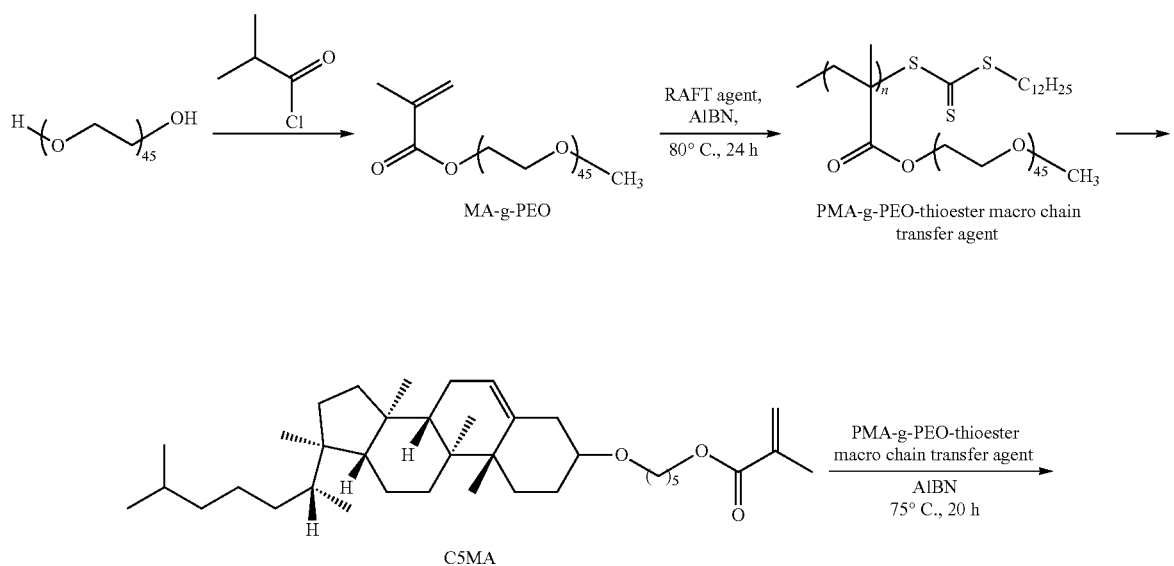

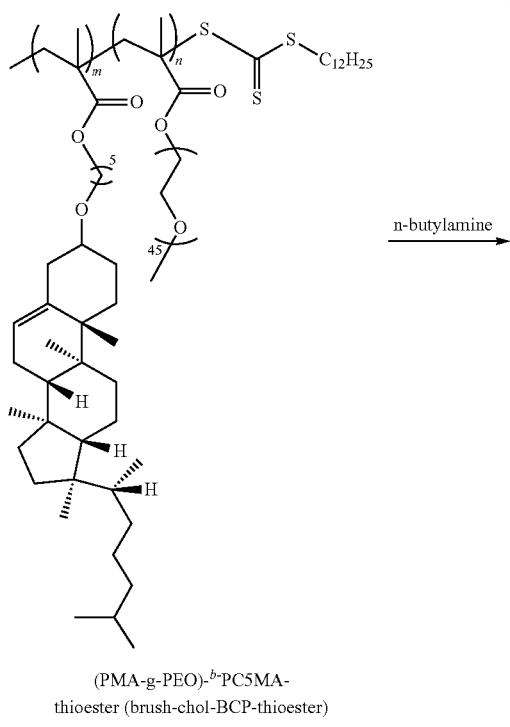

(PMA-g-PEO)-*b*-PC5MA-
thioester (brush-chol-BCP-thioester)

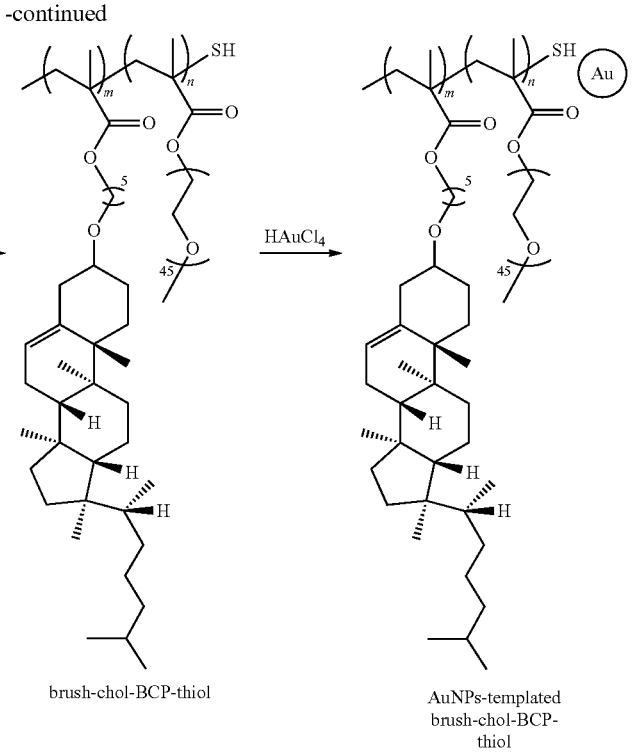

brush-chol-BCP-thiol

AuNPs-templated
brush-chol-BCP-
thiol methacrylate graft polyethylene oxide (MA-g-PEO): To synthesize macromonomer, MA-g-PEO, polyethylene oxide methyl ether (MW: 2000 Da, 4 g, 2 mmol) was dissolved in DCM, followed by addition of methacryloyl chloride and triethylamine (TEA) and stirred overnight under nitrogen. The molar ratio of PEO, methacryloyl chloride and TEA was 1:2:2. After 12 h, the insoluble salt (TEA.HCl) was filtered out, and the solution was collected. The macromonomer product was precipitated in excess cold diethyl ether and collected as light yellow solid. $^1$H NMR (CDCl$_3$, δ ppm): 6.15, 5.54 (m, 2H, CH$_2$—CH=COO—), 4.27 (t, 2H, —COOCH$_2$—, in PEO end group), 3.79-3.44 (m, —CH$_2$CH$_2$O—, repeating units of PEO), 3.36 (s, —OCH$_3$). $^{13}$C NMR (CDCl$_3$, δ ppm): 170.9 (—COO), 133, 126.6 (—CH$_2$, CH in vinyl group), 70.3 and 64.8 (—CH$_2$ repeat unit in PEO).

PEO macroinitiator (PMA-g-PEO-thioester): the PMA-g-PEO-thioester macro chain transfer agent was synthesized using RAFT polymerization. In a Schlenk tube equipped with a stir bar, macromonomer (MA-g-PEO, 0.5 g, 0.93 mmol), was dissolved in 1,4-dioxane (3 mL), followed by the addition of the RAFT agent (CTA, 18.3 mg, 0.05 mmol), and the initiator (AIBN, 0.82 mg, 0.005 mmol). The Schlenk tube was then degassed by three freeze-evacuate-thaw cycles and then placed in an oil bath maintained at 80° C. The reaction was allowed to proceed for 24 h. The reaction mixture was concentrated and precipitated in diethyl ether. The product was collected and dried in vacuum overnight. $^1$H NMR (CDCl$_3$, δ ppm): 4.27 (t, 2H, —COOCH$_2$—, in PEO end group), 3.79-3.44 (m, —CH$_2$CH$_2$O—, repeating units of PEO), 3.36 (s, —OCH$_3$), 3.2 (t, 2H, CH$_3$O$_{10}$H$_{20}$CH$_2$—S—), 1.60-1.75 (m, 6H, —S—C(CH$_3$)$_2$COO—), 1.25 (m, 20H, CH$_3$O$_{10}$H$_{20}$CH$_2$S—), 0.87 (t, 3H, CH$_3$O$_{10}$H$_{20}$CH$_2$S—). $^{13}$C NMR (CDCl$_3$, δ ppm): 170.9 (—COO), 133, 126.6 (—CH$_2$, CH in vinyl group), 74.5 (—COOCH—), 70.3 and 64.8 (—CH$_2$ repeat unit in PEO), 51.3-11.2 (—CH$_2$—C(CH$_3$)COO—). GPC (40° C., THF mobile phase, polystyrene standards): M$_n$=8950 g/mol, PDI=1.27.

P(PEO-b-C5MA)-thioester (Brush-chol-BCP-thioester; or (PMA-g-PEO)-b-PC5MA-thio ester): in a representative procedure, mixture of the PMA-g-PEO macro chain transfer agent (1.2 g, 0.2 mmol), C5MA (3.8 g, 28.0 mmol), and AIBN (6 mg, 0.04 mmol) were dissolved in 1,4-dioxane (3 mL) and degassed by performing three freeze-evacuate-thaw cycles. The reaction mixture was sealed and then placed in an oil bath maintained at 90° C. for 20 h. The resulting mixture was concentrated and precipitated in a large excess of methanol. The crude product was collected, Soxhlet extracted overnight using methanol to remove unreacted monomer, then extracted with THF and reprecipitated into methanol. The product, brush-chol-BCP-thioester, was collected and dried under vacuum. The thioester peak was appeared at 310 nm, as measured by UV-visible spectroscopy. $^1$H NMR (CDCl$_3$, δ ppm): 5.33 (d, 1H, —C=CH—, olefin group in cholesteryl moiety), 4.5 (m, 1H, —CH$_2$—COO—CH), 3.9 (m, 2H, —COOCH$_2$CH$_2$), 3.64 (m, —CH$_2$CH$_2$O— repeating units of PEO), 3.45 (m, 2H, —CH$_2$OCH—), 3.36 (s, —OCH$_3$), 3.2 (t, 2H, CH$_3$O$_{10}$H$_{20}$CH$_2$—S—), 2.50-0.55 (m, 56H, —CH$_3$, —CH$_2$—, —CH—, —CH—(OH$_3$)— in cholesteryl moiety, —CH$_2$—O(CH$_3$)COO—, —CH$_2$CH$_2$—CH$_2$CH$_2$CH$_2$— in spacer). $^{13}$C NMR (CDCl$_3$, δ ppm): 170.9 (—COO), 140.9 (—C=CH—, olefin group in cholesterol), 121.9 olefin group in cholesterol), 133, 126.6 (—CH$_2$, CH in vinyl group), 74.5 (—COOCH—), 70.3 and 64.8 (—CH$_2$ repeat unit in PEO), 51.3-11.2 (—CH$_2$—C(CH3)COO—, -cholesterol). GPC (40° C., THF mobile phase, polystyrene standards): M$_n$=18 320 g/mol, PDI=1.16.

P(PEO-b-C5MA)-thiol ((PMA-g-PEO)-b-PC5MA-thiol; or brush-chol-BCP-thiol: to obtain the brush-chol-BCP-thiol, the brush-chol-BCP-thioester was reduced by n-butylamine in THF. In a representative procedure, brush-chol-BCP-thioester (0.35 g, 0.02 mmol) and n-butylamine (80 mg, 1.1 mmol) were dissolved in THF under a blanket of nitrogen and stirred for 2 h until the color of solution changed from light yellow to colorless. The polymer was then precipitated in excess methanol. The crude product was collected; Soxhlet extracted overnight with methanol to remove unreacted monomer, and then extracted with THF, and finally reprecipitated into methanol. The product was collected and dried in vacuum. To establish the reaction kinetics, a solution of brush-chol-BCP-thioester in THF (1 mg/mL) was placed in a quartz cuvette fitted in the sample compartment of a UV-visible spectrometer. The appropriate amount of n-butylamine solution in THF was added and the absorbance of the solution at 310 nm was measured as a function of time. The structure was confirmed by $^1$H NMR and $^{13}$C NMR.

The formation of brush-chol-BCP-thiol was confirmed by FT-IR, indicating the thiol peak at 2450 cm$^{-1}$. In addition, $^1$H NMR spectroscopy showed the absence of the peak at 3.2 ppm corresponding to the protons of thioester groups for brush-chol-BCP-thiol, indicating that the thioester group was successfully substituted with the thiol group. In the UV-visible spectra, the original brush-chol-BCP-thioester exhibited a strong absorption centered at 310 nm, which belongs to the thioester group, while no absorption can be detected in this spectral region after the reduction. This result confirmed the formation of a thiol group in the brush-chol-BCP-thiol. Furthermore, the UV-visible spectra also provided kinetics for the reduction step by measuring the decrease with time of absorption at 310 nm upon injection of n-butylamine into brush-chol-BCP-thioester solution. The absorption intensity decreased rapidly upon addition of n-butylamine within 2 h and reached a low constant value, indicating that the reduction was completed with an efficiency >96%. Table 2 summarizes the molecular characterization of the brush-like block copolymers.

TABLE 2

Molecular characterization of as-synthesized brush-chol-BCPs polymers

| Polymer | $M_n$ (g/mol) GPC[a] | PDI[a] | Weight fraction[b] (%) PEO | C5A | Conversion (%) [c] |
|---|---|---|---|---|---|
| PEO macroinitiator (PMA-g-PEO thioester) | 8950 | 1.27 | 100 | — | 85 |
| P(PEO-b-C5MA)-thioester (Brush-chol-BCP-thioester) | 18 320 | 1.16 | 48 | 52 | 92 |
| P(PEO-b-C5MA)-thiol (Brush-chol-BCP-thiol) | 18 260 | 1.15 | 48 | 52 | 96[d] |

[a]Determined by GPC calibrated at 40° C. with THF as the mobile phase with polystyrene standards.
[b]The ratio of the integrals of peaks by $^1$H-NMR spectra at 5.33 ppm (olefin group in cholesteryl moiety) and 3.64 ppm (PEO repeating unit) is used to calculate the weight fraction of the brush-chol-BCPs.
[c] Conversion of monomer to polymer was determined using 1 H-NMR analysis.
[d] Conversion of reduction was determined using UV-visible spectra.

Example 3

Preparation and Characterization of Self-Assembled Nanoparticles and DOX-NPs with P(PEOA$_{SH}$-b-C5A) or with P(PEOA-b-C5MA)-SH The self-assembled nanoparticles based on P(PEOA$_{SH}$-b-C5A) were prepared by nanoprecipitation method. Briefly, P(PEOA$_{SH}$-b-C5A) (10 mg) were dissolved in THF (2 mL), followed by the dropwise injection into distilled water (10 mL) containing Tween® 80 (1%, w/v) under homogenization at 20,000 rpm. THF was then evaporated under a flow of nitrogen at ambient temperature. The nanoparticles were collected by ultra-centrifugation at 50,000 rpm for 60 min to remove Tween® 80, followed by dispersion into distilled water. The same procedure was used to prepare the P(PEOA-b-C5A)-SH nanoparticles.

The Critical Aggregation Concentration (CAC) was determined by the fluorescence technique using pyrene as a hydrophobic probe. The pyrene solution (3×10$^{-4}$ M) in acetone was added into the test tubes, and followed by evaporation to remove the organic solvent. Then, various concentrations of copolymer solution in distilled water (10 mL) were added to the test tubes and sonicated for 3 h at 60° C. to equilibrate the pyrene and the nanoparticles. The concentration of sample solution was varied from 0.005 to 0.5 mg/mL. The final concentration of pyrene was 6.0× 10$^{-7}$M. The emission spectra of pyrene were recorded in the range of 350-450 nm using a fluorescence spectrophotometer (Perkin Elmer LS-55B, USA) at the excitation wavelength of 336 nm. For the measurement of the intensity ratio of the first (374.5 nm) and the third highest energy bands (386 nm) in the pyrene emission spectra, the slit opening for the excitation and emission spectra was set at 2.5 nm.

A linear decrease was observed with the increase in the LCPs concentration. Based on this protocol, the CAC value of P(PEOA$_{SH}$-b-C5A$_{13}$) copolymer was lower than that of P(PEOA$_{SH}$-b-PC5A$_{36}$) copolymers, showing the values of 9.4, and 15.8 (Table 3), respectively, indicating a stronger hydrophobic interaction in the inner core of P(PEOA$_{SH}$-b-PC5A$_{36}$) nanoparticles with higher cholesterol content. The CMC value of thiol functionalized copolymer P(PEOA-b-C5A)-SH was 15.2 (Table 3.) These low CAC values of brush-chol-BCPs suggested that the brush-chol-BCPs are desirable for systemic drug delivery and may circulate as self-assembled nanoparticles in vivo for an extended period of time.

TABLE 3

Characterization of self-assembled brush-chol-BCPs and dual-encapsulated nanoparticles

| Samples | CAC (mg/L) | DOX•HCl feed ratio (%) | DLC (%) | EE (%) | Average size (nm) | PDI |
|---|---|---|---|---|---|---|
| P(PEOA$_{SH}$-b-C5A$_{36}$) | 15.6 ± 0.8 | | | | 128.5 ± 5.6 | 0.08 |
| P(PEOA$_{SH}$-b-C5A$_{13}$) | 9.4 ± 0.6 | | | | 175.3 ± 5.1 | 0.09 |

TABLE 3-continued

Characterization of self-assembled brush-chol-BCPs and dual-encapsulated nanoparticles

| Samples | CAC (mg/L) | DOX•HCl feed ratio (%) | DLC (%) | EE (%) | Average size (nm) | PDI |
|---|---|---|---|---|---|---|
| P(PEOA$_{SH}$-b-C5A$_{36}$)-Au | | | | | 158.4 ± 4.4 | 0.21 |
| P(PEOA$_{SH}$-b-C5A$_{13}$)-Au | | | | | 202.6 ± 6.9 | 0.28 |
| P(PEOA$_{SH}$-b-C5A$_{36}$)-DOX-Au | | 25 | 23.8 | 95.2 | 183.8 ± 5.5 | 0.25 |
| P(PEOA$_{SH}$-b-C5A$_{13}$)-DOX-Au | | 25 | 17.7 | 70.8 | 230.2 ± 8.9 | 0.31 |
| P(PEOA-b-C5MA)-SH | 15.2 ± 0.2 | | | | 109.3 ± 7.3 | 0.05 |
| P(PEOA-b-C5MA)SH-Au | | | | | 122.5 ± 9.1 | 0.09 |
| P(PEOA-b-C5MA)-SH-DOX | | 25 | 15.7 | 62.8 | 133.7 ± 7.9 | 0.08 |
| P(PEOA-b-C5MA)-DOX-Au | | 25 | 21.4 | 85.6 | 157.3 ± 6.5 | 0.1 |

CAC: critical aggregation concentration, measured by the probe fluorescence technique
DLC: drug loading content = (amount of DOX in nanoparticle/amount of DOX-loaded nanoparticle) × 100
EE: encapsulation efficiency = (amount of DOX in nanoparticle/amount of DOX used for nanoparticle preparation) × 100

Example 4

Preparation and Characterization of Dual-Loaded Nanoparticles with P(PEOA$_{SH}$-b-C5A) or with P(PEOA-b-C5MA)-SH To prepare Au NP-encapsulated P(PEOA$_{SH}$-b-C5A), in a 50 mL round-bottomed flask equipped with a condenser, 10 mL of 0.01 wt % HAuCl$_4$ in DI water was first heated to a boil with vigorous stirring. Next, 0.2 mL of 1 wt % sodium citrate in DI water was added quickly, which resulted in a color change from blue to burgundy. After further stirring at the same temperature for 10 min, the resulting solution was cooled to room temperature with continuous stirring yielding citrate-capped Au NPs. The P(PEOA$_{SH}$-b-C5A) solution (10 mg in 2 mL THF) was injected with a dropwise fashion in Au NPs solution containing Tween® 80 (1%, w/v) over 15 min. The solution was then stirred at room temperature for 2 h to allow for complete exchange of the citrate molecules with the thiol group of PEO. The resulting solution was centrifuged at 3000 rpm for 10 min to remove precipitated Au NPs. The same procedure was used to prepare the dual-loaded P(PEOA-b-C5MA)-SH nanoparticles.

To prepare dual-encapsulated nanoparticles, DOX.HCl was first dissolved in DMF containing 2 equivalence of TEA and stirred overnight in the dark to form hydrophobic DOX. The organic solvent was removed by vacuum dryer to obtain dried hydrophobic DOX. The hydrophobic DOX were dissolved in THF, and the solution was injected dropwise into Au NP-encapsulated brush-chol-BCPs solution under homogenization at 20,000 rpm. The resulting solution was centrifuged at 3000 rpm for 10 min, followed by the filtration through 0.45 µm syringe to remove any precipitated free DOX. The final products were obtained after ultra-centrifugation and lyophilization. The average particle size and size distribution of the dual-encapsulated nanoparticles (1 mg/mL) were measured using a dynamic light scattering (DLS) instrument (Malvern). The morphologies of dual-encapsulated nanoparticles were imaged by Tecnai Biotwin G2 transmission electron microscopy (TEM) with accelerating voltage of 80 KV. Specimens were prepared by dropping solution of the nanoparticles on to copper grid coat with Formvar film, followed by air-drying.

The amount of DOX in the dual-encapsulated nanoparticles was determined by a colorimetric method. The lyophilized dual-encapsulated nanoparticles (0.5 mg) were dissolved in THF (2 mL) to obtain clear solutions. The absorbance at 480 nm was detected with a UV-VIS spectrophotometer. DOX standard solutions were prepared at various concentrations and the absorbance at 480 nm was measured to generate the calibration curve for calculating the drug-loading content. The drug-loading content (DLC) and encapsulation efficiency (EE) were calculated by the following equations:

$$DLC = \frac{\text{Amount of } DOX \text{ in nanoparticles}}{\text{Amount of } DOX\text{-loaded nanoparticles}} \times 100$$

$$EE = \frac{\text{Amount of } DOX \text{ in nanoparticles}}{\text{Amount of } DOX \text{ used for nanoparticle preparation}} \times 100$$

Nanocarriers that are administered through the intravenous route encounter interactions with serum proteins, the major species in the blood components that may alter the stability and the tissue distribution of the carriers. Thus, if the nanocarriers maintain their integrity when encountering serum proteins, efficient drug delivery to the target tissue can be expected. For stability test, lyophilized dual-encapsulated nanoparticles were suspended in phosphate-buffered saline (PBS)/fetal bovine serum (FBS) (1:1) at concentration of 1 mg/mL, followed by sonication for about 10 min and filtration through 0.45 µm syringe filter membrane. The particle size of the nanoparticles was monitored over the storage at 4° C. using a Zetasizer (Malvern).

Results

Figure 3:
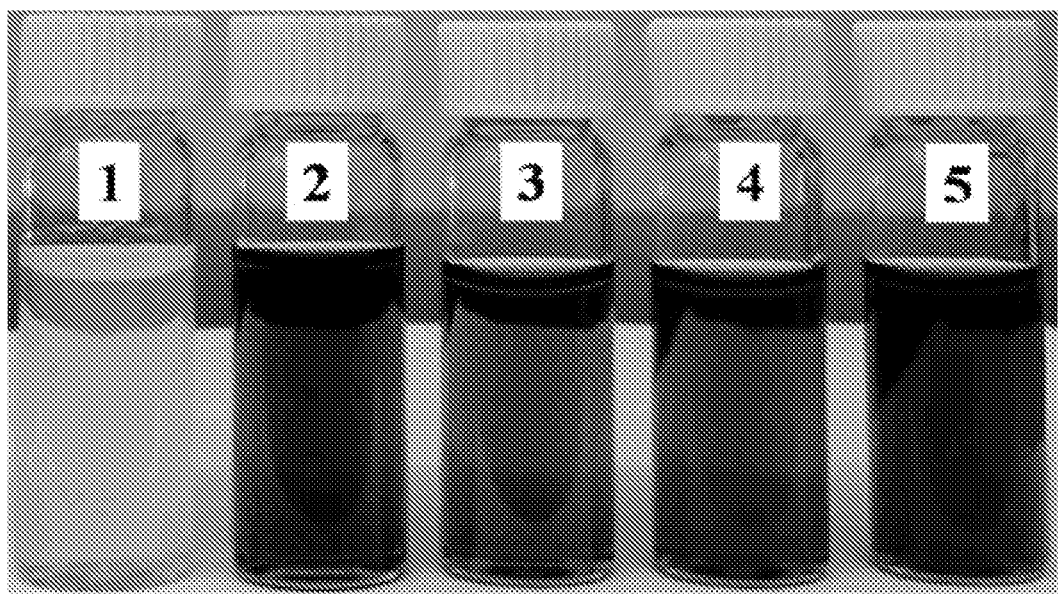
FIG. 3 shows self-assembled and dual-encapsulated brush-chol-BCPs nanoparticles at concentration of 1 mg/mL. The red color of dual-encapsulated nanoparticles is darker than Au NP-encapsulated P(PEOA-b-PC5MA)-SH nanoparticles, indicative of the presence of DOX. 1: blank NPs in water; 2: AuNPs-templated brush-chol-BCP in DMF; 3: AuNPs-encapsulated NPs in water; 4: DOX-encapsulated NPs in water; and 5: dual-encapsulater NPs in water

Without being bound to a particular theory, it is believed that the nanoparticles likely have a core/shell structure bearing a hydrophobic cholesterol inner core that could serve as a reservoir for hydrophobic drugs, and a hydrophilic PEO shell containing thiol groups. It is believed that Au NPs produced in solution phase could be deposited at brush-chol-BCPs interface due to interaction between Au and thiol groups. Au NPs were successfully encapsulated into brush-chol-BCPs, as confirmed by TEM (see FIGS. 3 and 4). The Au NP-loaded brush-chol-BCPs appeared as darker spherical nanoparticles in the TEM image compared to the nanoparticles without Au NP due to higher density of the metal nanoparticles. In addition, the energy dispersive X-ray (EDX) spectrum with peaks at 2.1 keV revealed the presence of Au within the self-assembled brush-chol-BCPs (data not shown).

Furthermore, hydrophobic DOX molecules were successfully encapsulated into Au NP-encapsulated brush-chol-BCPs through hydrophobic interactions between DOX and cholesterol moieties. With the DOX feed ratio of 25% (w/w), high drug loading content (DLC) of 23.8% (w/w) in P(PEOA$_{SH}$-b-PC5A$_{36}$) nanoparticles could be achieved with high encapsulation efficiency (EE) of 95.2%. The drug loading was affected by the molecular weight of the brush-chol-BCPs; for example, the P(PEOA$_{SH}$-b-PC5A$_{13}$) with less hydrophobic block yielded lower drug loading level of 19.3% (w/w) and larger particle size (~200 nm). Without being bound to a particular theory, it is believed that this could be attributed to the change in balance between the hydrophilic and hydrophobic segments in the self-assembled nanoparticles, and this in turn affects interaction of the hydrophobic core with DOX. Due to the intramolecular interaction and entanglement properties of cholesterol side chain, the hydrophobic interaction within brush-chol-BCPs can enhance stability, which will be beneficial to the nanoparticles for systemic drug delivery. In addition, both the inter- and intramolecular hydrophobic interactions in these polymers have a positive influence on drug encapsulation, leading to improved drug loading capacity and efficiency. The drug loading capacity also was affected significantly by the presence of cholesterol moieties due to excellent cholesterol-DOX compatibility.

Figure 4A:
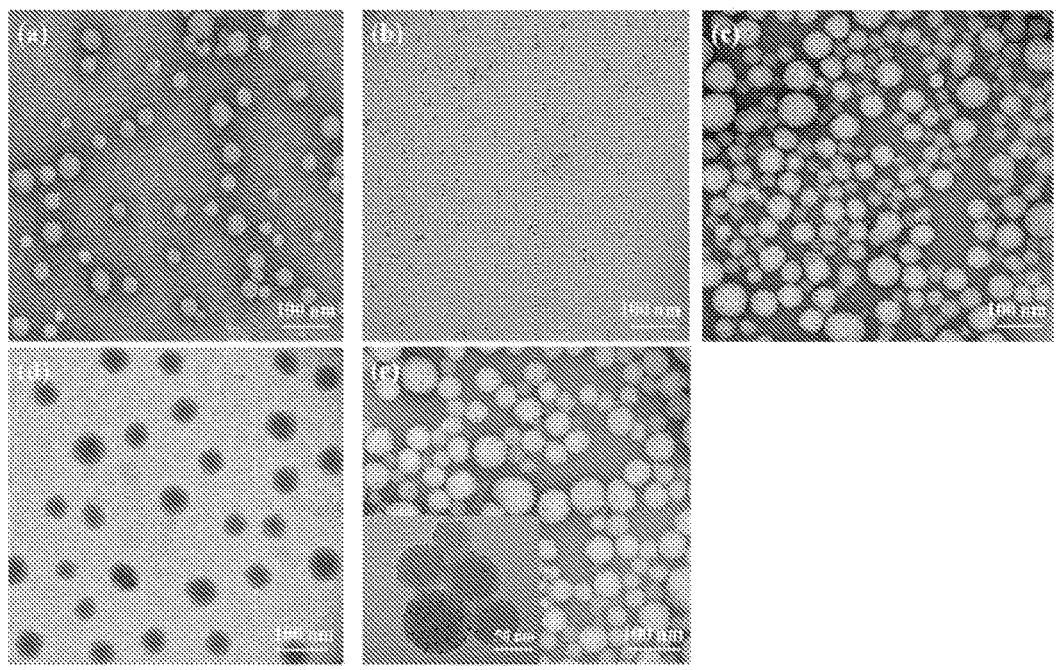
FIG. 4A shows transmission electron microscopy (TEM) images of self-assembled and dual-encapsulated brush-chol-BCPs, P(PEOA-b-PC5A)-SH: (a) blank brush-chol-BCPs nanoparticles, (b) AuNPs-templated brush-chol-BCP in DMF, (c) Au NP-encapsulated brush-chol-BCPs, (d) DOX-encapsulated NPs in water, and (d) dual Au NPs+DOX-encapsulated brush-chol-BCPs; scale bars are 100 nm. The TEM images showed that the brush-chol-BCPs nanoparticles were spherical in shape with uniform sizes distribution.
Figure 4B:
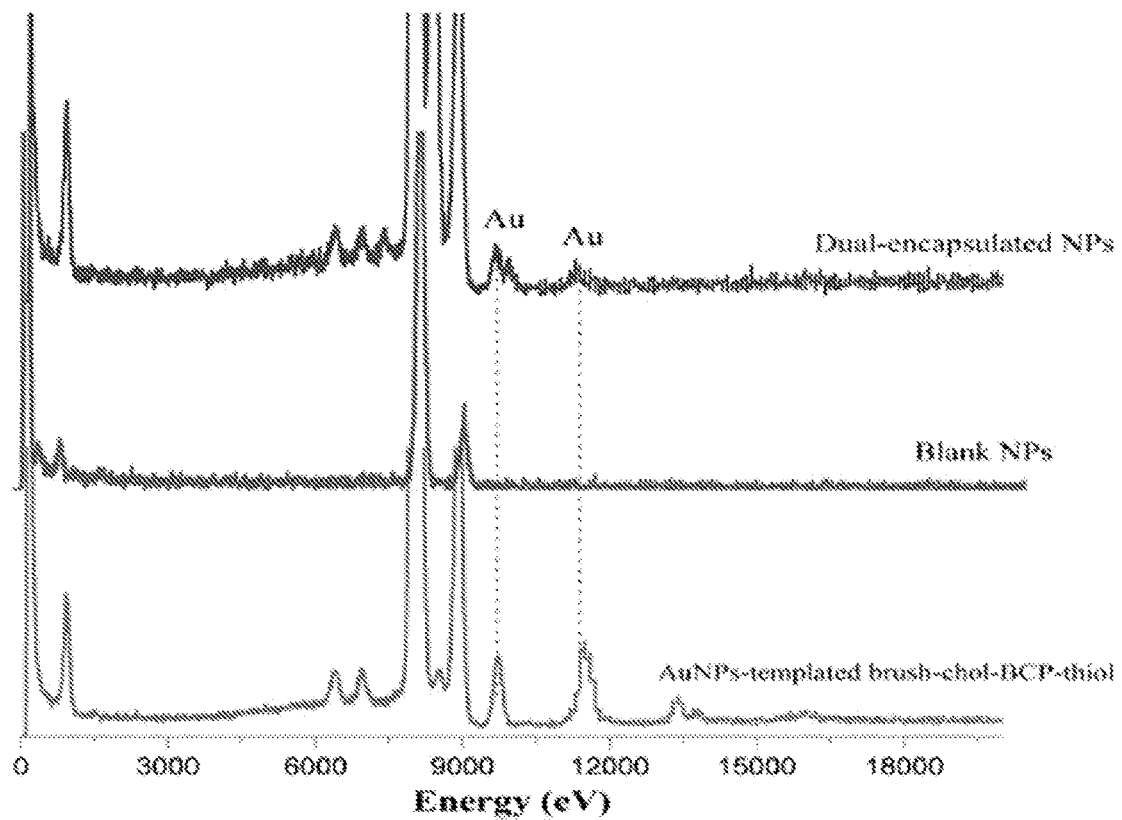
FIG. 4B shows the energy dispersive X-ray (EDX) spectroscopy of AuNPs within AuNP-templated brush-chol-BCP and dual-encapsulated NPs.
Figure 5:
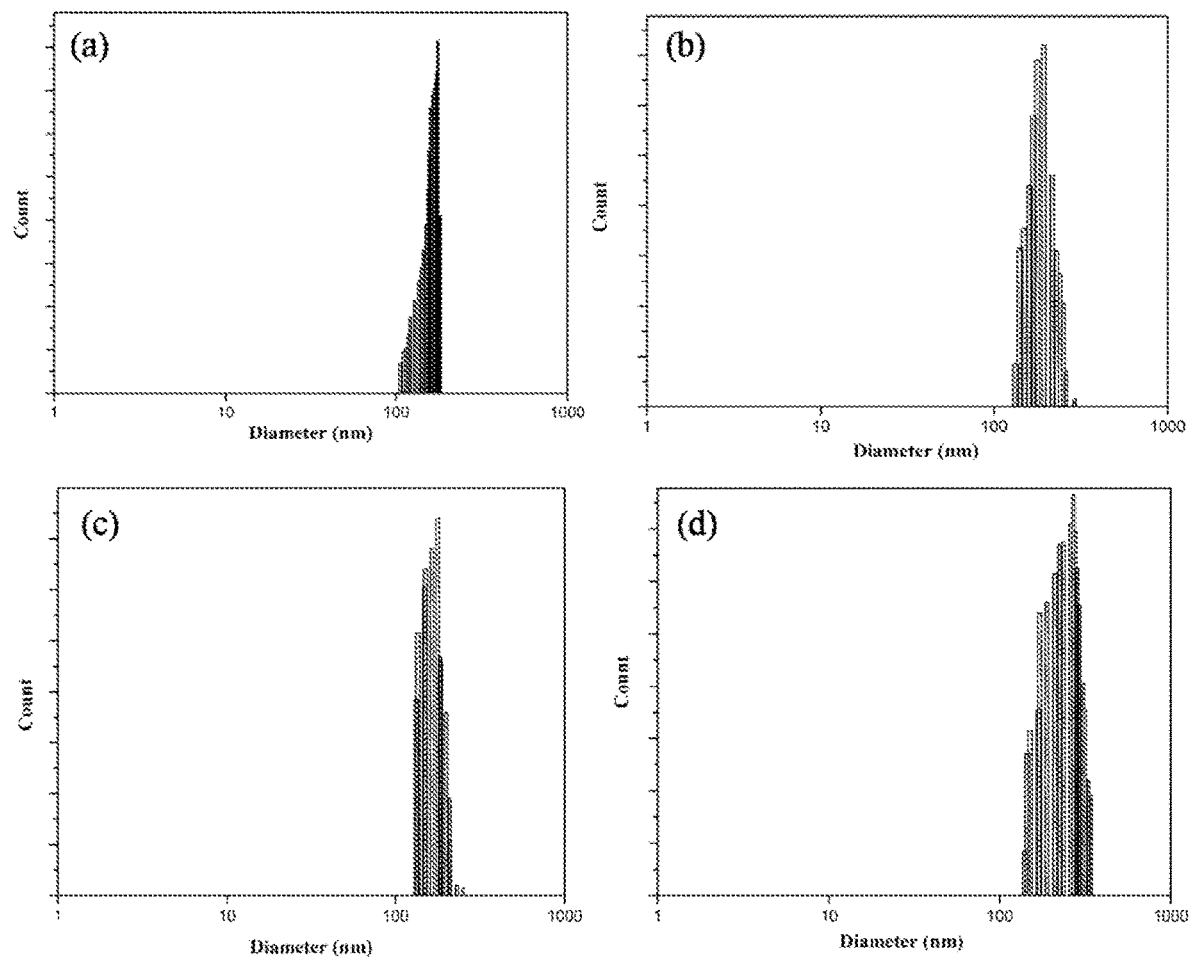
FIG. 5 illustrates size distribution of brush-chol-BCPs nanoparticles before (a, c) and after (b, d) dual-encapsulated: (a, b) P(PEOA$_{SH}$-b-PC5A$_{36}$), and (c, d) P(PEOA$_{SH}$-b-C5A$_{13}$), by dynamic light scattering (DLS) measurements at 25° C.

The average particle size of brush-chol-BCPs nanoparticles ranged from 128 to 175 nm with narrow size distribution (PDI less than 0.1) (Table 3). The nanoscale size and narrow unimodal PDI indicate that the brush-chol-BCPs assembled nanoparticles possess good physical attributes as a nanocarrier for encapsulation of Au NPs and DOX. The average size of the nanoparticles decreased with increasing cholesterol content due to the formation of a more compact hydrophobic inner core. The TEM images showed that the nanoparticles brush-chol-BCPs assembled nanoparticles were spherical in shape with sizes of 100-170 nm for blank nanoparticles, and bigger sizes of 150-200 nm for Au NP-encapsulated nanoparticles (FIG. 4), which was slightly smaller than the size measured by DLS. Physical encapsulation of DOX increased particle size and polydispersity of the nanoparticles, showing sizes of 230.2 nm, and 183.8 for dual-encapsulated P(PEOA$_{SH}$-b-PC5A$_{13}$), and P(PEOA$_{SH}$-b-PC5A$_{36}$), respectively (FIG. 5). The nanoparticles with dual-encapsulated Au NPs+DOX were spherical in shape with sizes of 182-230 nm, as shown by TEM images (FIG. 4). Particle size is of importance in the consideration of in vivo applications as it would influence the biodistribution of the nanoparticles. Nanoparticles smaller than 200 nm in diameter preferentially accumulate and reside in tumor masses via the enhanced permeability and retention (EPR) effect, whereas drug carriers with larger diameters are readily scavenged by the reticuloendothelial system (RES).

Figure 6A:
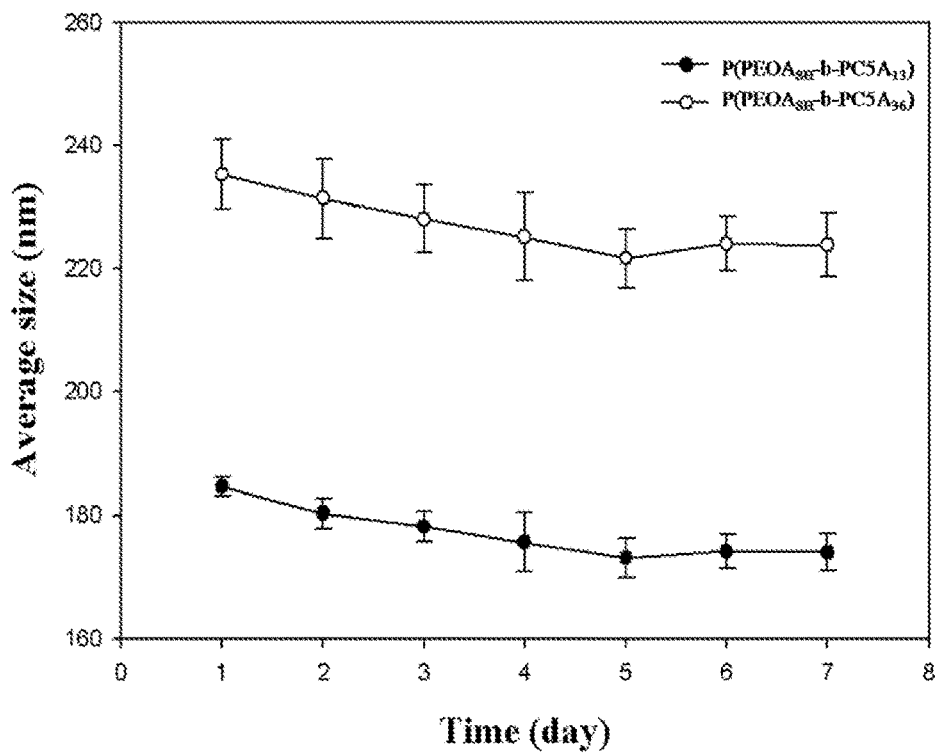
FIG. 6A shows stability of dual-encapsulated P(PEOA$_{SH}$-b-PC5A$_{36}$) and P(PEOA$_{SH}$-b-C5A$_{13}$) nanoparticles in PBS/FBS (1:1) stored at 4° C.
Figure 6B:
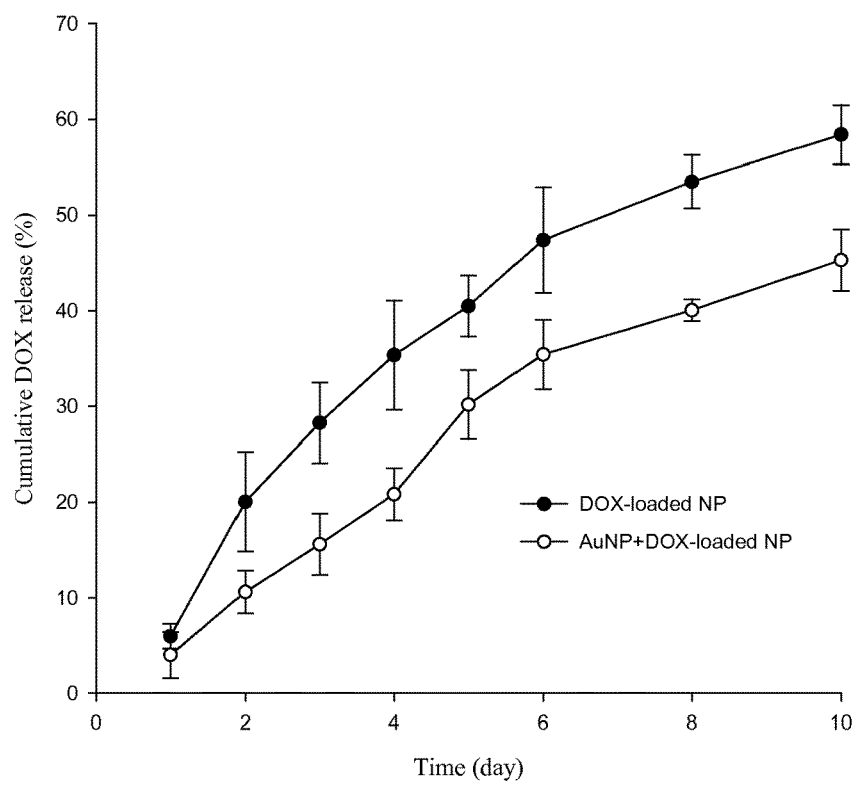
FIG. 6B shows release profiles of DOX-loaded P(PEOA$_{SH}$-b-PC5A) nanoparticles in PBS (pH 7.4).
Figure 6C:
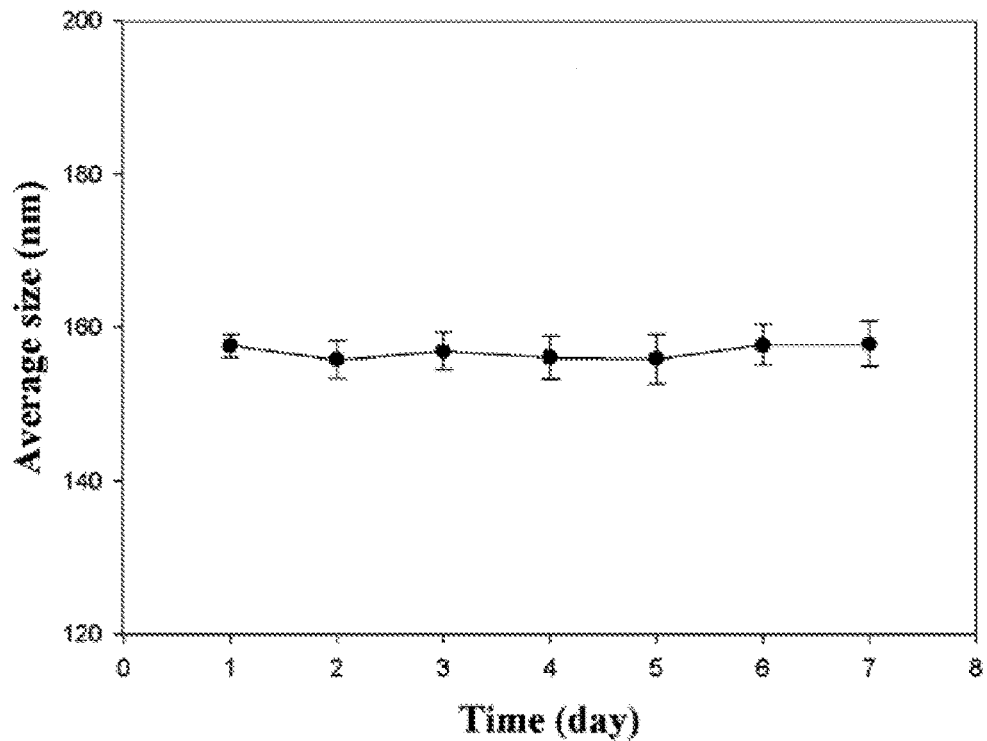
FIG. 6C shows stability of dual-encapsulated P(PEO-b-PC5MA)-SH nanoparticles in PBS/FBS (1:1) stored at 4° C.
Figure 6D:
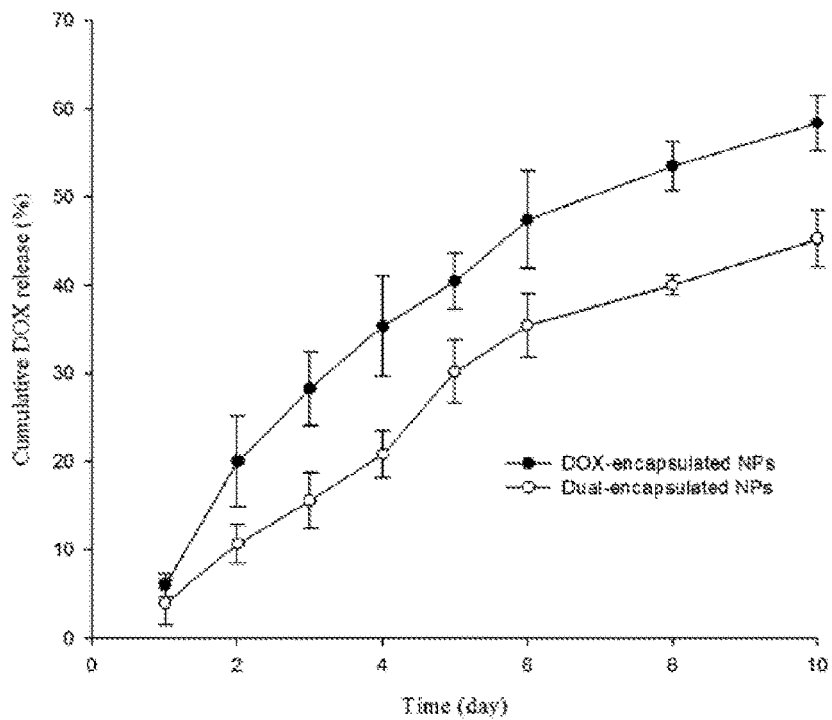
FIG. 6D shows release profiles of DOX-loaded and dual-loaded P(PEOA-b-PC5MA)-SH nanoparticles in PBS (pH 7.4).

To investigate the physical stability of the dual-encapsulated nanoparticles, the DLS was used to monitor the size change of the nanoparticles in phosphate-buffered saline (PBS)/fetal bovine serum (FBS) solution. The average particle size of the dual-encapsulated nanoparticles did not change significantly after 1 week storage at 4° C. in 50% FBS (FIGS. 6A and 6C), and no precipitation or aggregation was observed, indicating that excellent stability was achieved by hydrophobic interactions between cholesterol molecules and/or between cholesterol, Au NPs and DOX. This finding indicates that the dual-encapsulated brush-chol-BCPs nanoparticles are stable and retain their forms and structures in aqueous media and are suitable for in vivo applications.

Example 5

Synthesis and Purification of P(NBCh9-b-NBPEG)

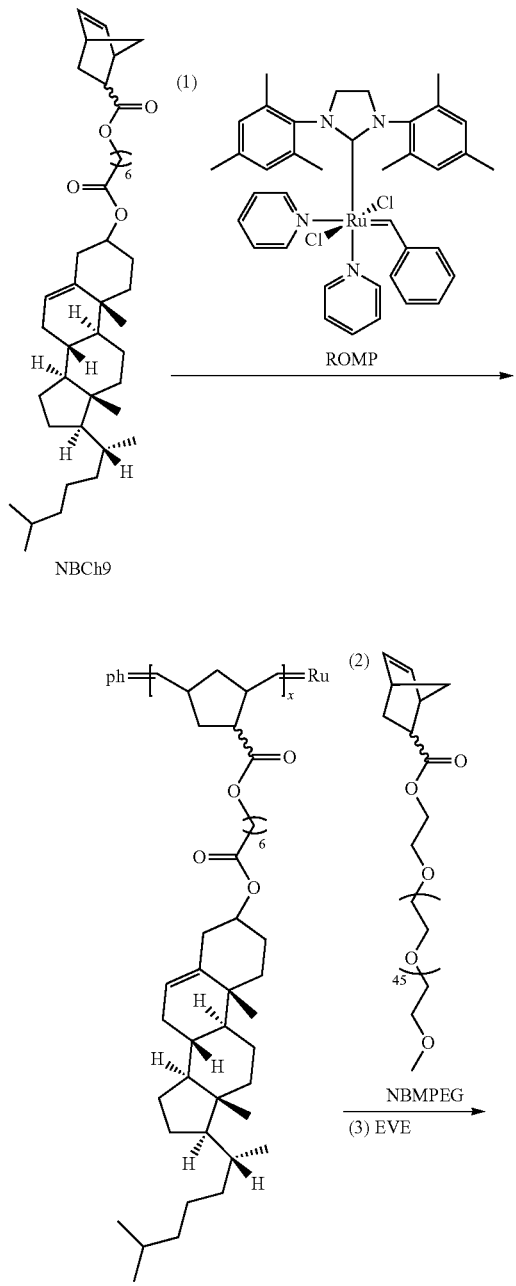

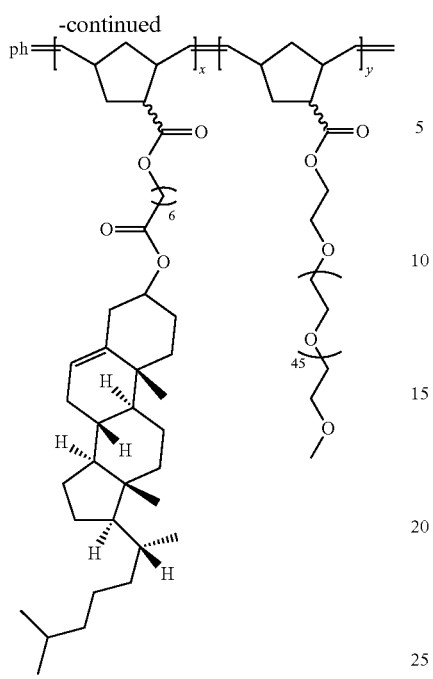

Synthesis of norbornene functionalized monomers, 5-{9-(cholesteryloxycarbonyl)-nonyloxycarbonyl}-bicyclo[2.2.1]hept-2-ene (NBCh9) and Methoxy polyethylene glycol (MPEG) ($M_n$=2 Kg/mol) functionalized norbornene (NBPEG) were reported previously. All block copolymers were synthesized using ring opening metathesis polymerization (ROMP) as described in Deshmukh, P., et al. (*Macromolecules* 2013, 46, 8245-8252), which is incorporated by reference herein. Table 4 summarizes the molecular characterization of the brush-like block copolymers.

TABLE 4

Molecular characterization of P(NBCh9)x-b-(NBPEG)y

| Polymer[a] | $M_n$[b] kg/mol | | | Weight fraction (%)[c] | |
| --- | --- | --- | --- | --- | --- |
| | theoretical | GPC | PDI | NBCh9 | NBMPEG |
| 400 kDa-50  P(NBCh9)$_{50}$-b-(NBMPEG)$_{170}$ | 400 | 126 | 1.24 | 7.7 | 92.3 |
| 600 kDa-75  P(NBCh9)$_{75}$-b-(NBMPEG)$_{255}$ | 600 | 216 | 1.16 | 5.7 | 94.3 |
| 600 kDa-180 P(NBCh9)$_{180}$-b-(NBMPEG)$_{222}$ | 600 | 118 | 1.16 | 18 | 82 |

[a]number in subscript represents theoretical degree of polymerization, 400 kDa-50 contained ~8% w/w of cholesterol content while 600 kDa-75 and 600 kDa-180 contained ~6% and 18% w/w of cholesterol content, respectively;
[b]molecular weight determined using GPC,
note:
observed molecular weights are lower than theoretically calculated due to the brush architecture;
[c]weight fraction percent of monomer is determined by $^1$H-NMR integration of peaks for cholesterol and PEG side chains, respectively.

Additional brush-like block copolymers were prepared according to this method and the results are summarized in Table 4A. These block copolymers are also able to form nanostructures.

TABLE 4A

Molecular characterization of P(NBCh9)x-b-(NBPEG)y

| Polymer[b] | $M_n$ kg/mol | | | Weight fraction (%)[c] | |
| --- | --- | --- | --- | --- | --- |
| | theoretical[d] | GPC[e] | PDI[e] | NBCh9 | NBMPEG |
| P(NBCh9)$_{125}$[a] | 84 | 61 | 1.09 | 100 | — |
| P(NBCh9)$_{135}$-b-(NBMPEG)$_{15}$ | 122 | 74 | 1.06 | 78 | 22 |
| P(NBCh9)$_{80}$-b-(NBMPEG)$_{20}$ | 96 | 41 | 1.17 | 55 | 45 |
| P(NBCh9)$_{65}$-b-(NBMPEG)$_{35}$ | 119 | 48 | 1.20 | 28 | 75 |
| P(NBCh9)$_{35}$-b-(NBMPEG)$_{65}$ | 163 | 72 | 1.24 | 16 | 84 |
| P(NBCh9)$_{25}$-b-(NBMPEG)$_{85}$ | 201 | 92 | 1.20 | 7 | 93 |
| P(NBMPEG)$_{50}$[a] | 108 | 69 | 1.12 | — | 100 |

[a]PNBCh9 and PNBMPEG represent homopolymer of NBCh9 and NBMPEG (macro)monomer, respectively, reported from previous publications.
[b]Subscript represents the degree of polymerization calculated based on monomer to catalyst ratio.
[c]Determined by 1H NMR analyses.
[d]Theoretical molecular weight determined by $^1$H-NMR integration of peaks for cholesterol and PEG side chains, respectively.
[e]Determined by GPC with RI detector, where THF was used as eluent and polystyrene standards were used to construct a conventional calibration.

Example 6

Preparation and Characterization of Self-Assembled Nanoparticles and DOX-NPs Blank self-assembled nanoparticles were prepared by a dialysis method. Briefly, the P(NBCh9-b-NBPEG) was dissolved in DMF with the aid of sonication. The solution was then transferred to a dialysis bag (MWCO: 10,000 Da) and dialyzed against distilled water for 48 h. To prepare DOX-loaded P(NBCh9-b-NBPEG) nanoparticles (DOX-NPs), DOX.HCl was first dissolved in DMF containing 2 equivalents of TEA and stirred overnight in the dark to form hydrophobic DOX and TEA.HCl. Each copolymer was added, and then the solution was stirred for another hour in the dark. The solution was then dialyzed against distilled water for 48 h to remove free DOX and solvents. The precipitated DOX was removed by centrifugation at 8000 rpm for 10 min, followed by filtration through 0.45 μm syringe. The final products were collected after lyophilization.

The average particle size, size distribution and zeta-potential of the DOX-NPs (1 mg/mL) were measured using a dynamic light scattering (DLS) as described in Example 4. The Critical Aggregation Concentration (CAC) of the P(NBCh9-b-NBPEG) copolymers was determined by fluorescence measurements using pyrene as a hydrophobic probe as described in Example 3. The slit opening for the excitation and emission spectra was set at 5 nm. The amount of DOX-loaded into nanoparticles was determined by a colorimetric method as described in Example 4.

Results

Three amphiphilic P(NBCh9-b-NBPEG) brush-like copolymers of MW 400 kDa (400 kDa-50) and 600 kDa (600 kDa-75 and 600 kDa-180) readily self-assembled in aqueous solution to form nanoparticles due to the hydrophobic interaction between the cholesterol moieties. The CAC, which is the threshold concentration of self-aggregation formation, was determined by the intensity ratio for the two fluorescence emission peaks (1374/1385) of pyrene. A linear decrease was observed with an increase in the P(NBCh9-b-NBPEG) concentration. The CAC value of the 400 kDa-50 copolymer was lower than that either of the 600 kDa copolymers containing cholesterol (Table 4) indicating greater stability of the 400 kDa-50 copolymer. At the same molecular weight, the 600 kDa copolymer with the higher cholesterol content (600 kDa-180) had a greater CAC value than the 600 kDa copolymer with the lower cholesterol content (600 kDa-75), indicating a stronger hydrophobic interaction in the inner core of the P(NBCh9-b-NBPEG) nanoparticles with higher cholesterol content. These CAC values were in the typical range of PEG-based block copolymers, indicating that the P(NBCh9-b-NBPEG) copolymers may circulate as self-assembled nanoparticles in vivo for an extended period of time. Without being bound to a particular theory, it is believed that the nanoparticles likely have a core/shell structure bearing a hydrophobic cholesterol inner core that could serve as a reservoir for hydrophobic drugs.

The hydrophobic DOX was successfully encapsulated into the P(NBCh9-b-NBPEG) self-assembled nanoparticles using a dialysis method. With a DOX feed ratio of 25% (w/w), DLC in the 400 kDa-50 nanoparticles was about 22.1% with EE of 88.4%. The drug loading was affected by the molecular weight of the copolymers. Despite having higher cholesterol content than the 400 kDa-50 copolymer, the DLC and EE values were lower in the 600 kDa-180 copolymer (Table 5). This could be attributed to the change in balance between the hydrophilic and hydrophobic segments of the 600 kDa-180 resulting in different self-assembly behavior of the nanoparticles. The 600 kDa-180 copolymer with the higher cholesterol content had slightly greater DLC and EE values than the 600 kDa-75.

TABLE 5

Characterization of P(NBCh9-b-NBMPEG) and DOX-NPs

| Samples | CAC (mg/L) | DOX•HCl feed ratio (%) | DLC (%) | EE (%) | Average size (nm) | PDI | Zeta potential (mV) |
|---|---|---|---|---|---|---|---|
| 400 kDa-50 | 5.4 ± 0.2 | | | | 124.2 ± 5.2 | 0.09 | −18.8 ± 0.7 |
| 600 kDa-75 | 21.1 ± 0.5 | | | | 179.1 ± 3.2 | 0.05 | −14.9 ± 0.1 |
| 600 kDa-180 | 15.9 ± 0.3 | | | | 144.4 ± 2.1 | 0.04 | −6.9 ± 0.8 |
| 400 kDa-50-DOX | | 25 | 22.1 | 88.4 | 138.3 ± 4.3 | 0.20 | −3.1 ± 0.2 |
| 600 kDa-75-DOX | | 25 | 17.2 | 68.8 | 197.5 ± 1.5 | 0.16 | −1.6 ± 0.2 |
| 600 kDa-180-DOX | | 25 | 19.8 | 79.2 | 189.4 ± 4.1 | 0.15 | −0.7 ± 0.1 |

DLC: drug loading content
EE: encapsulation efficiency

Figure 7:
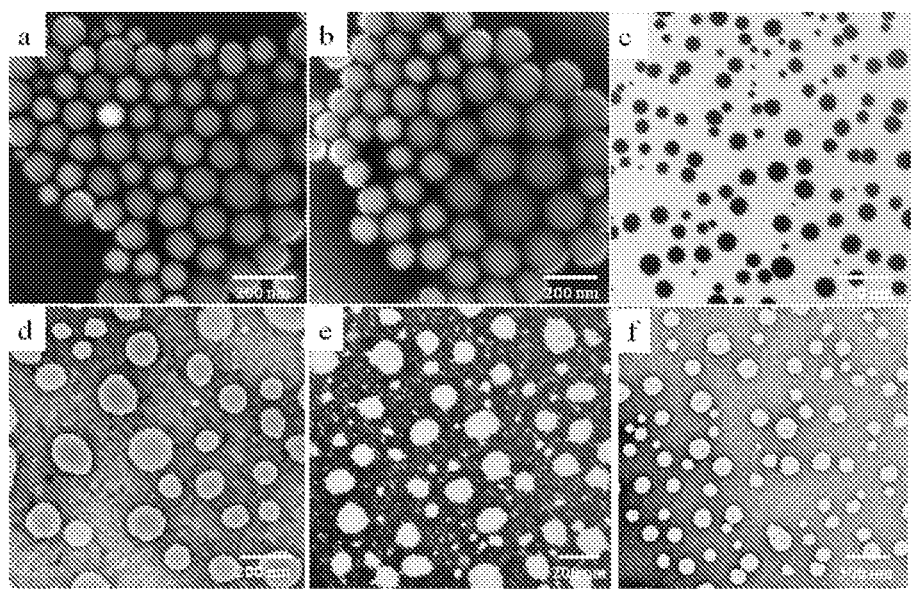
FIG. 7 shows TEM images of 400 kDa-50 (a), 600 kDa-75 (b), 600 kDa-180 (c), 400 kDa-50-DOX (d), 600 kDa-75-DOX (e), and 600 kDa-180-DOX (f). Nanoparticles in (a), (b), (d), (e), and (f) images were negatively stained with 1% phosphoric tungstic acid.

The particle size and morphology of blank P(NBCh9-b-NBMPEG) nanoparticles and DOX-NPs were measured by DLS and TEM, respectively. The average particle size of blank P(NBCh9-b-NBPEG) nanoparticles ranged from 124 to 179 nm with a narrow size distribution (PDI less than 0.1) (Table 5). The average size of the nanoparticles increased with increasing molecular size from 400 kDa to 600 kDa. At the same MW of 600 kDa, the nanoparticle size decreased with increasing cholesterol content due to the formation of a more compact hydrophobic inner core. Physical encapsulation of DOX increased particle size and polydispersity of the nanoparticles (Table 5). The TEM images showed that the nanoparticles with and without DOX loading were spherical in shape with diameters of 100-160 nm for blank nanoparticles and 120-170 nm for DOX-NPs (FIG. 7). The particle sizes determined by TEM were slightly smaller than the size measured by DLS. Particle size is of importance in the consideration of in vivo applications as it influences the biodistribution of the nanoparticles, with the ideal size for self-assembled nanoparticles to accumulate in tumor tissue via the EPR effect is less than 200 nm. Therefore, the nano-scaled particle sizes 200 nm) of the DOX-NPs are favorable for passive tumor targeting via the EPR effect. Owing to the pendant carbonyl hydroxyl group of the cholesterol derivative, the 400 kDa-50, 600 kDa-75, and 600 kDa-180 nanoparticles were negatively charged at their surface, as reflected in the zeta-potential values of −18.8, −14.9, and −6.9 mV for 400 kDa-50, 600 kDa-75, and 600 kDa-180, respectively (Table 5). To efficiently deliver the drug to a targeted tumor site, nanoparticles must have ability to remain in the blood stream for a considerable time without being eliminated by mononuclear phagocyte system (MPS). This ability depends on their size and surface characteristics. It is well-known that nanoparticles having hydrophilic surfaces can escape macrophage capture with reports that the negatively charged liposomes with approximately 200 nm in diameter showed an increased rate of liver uptake compared to the neutral liposomes. The reduction of negative charge from −40 mV to −15 mV led to a significantly reduced rate of liver uptake and prolonged blood circulation. Therefore, the DOX-NPs with its hydrophilic surface and neutral surface charge are suitable for hindering plasma protein adsorption and clearance by the MPS.

Example 7

Stability and In Vitro Release of DOX from the Nanoparticles

Lyophilized DOX-NPs (1 mg/mL) were suspended in the serum-containing phosphate-buffered saline (PBS) solution (50% FBS), followed by sonication for 10 min and filtration through a 0.45 μm syringe filter membrane. The particle size of the nanoparticles stored at 4° C. was monitored over the storage time using a Malvern Zetasizer.

In vitro release of DOX from the nanoparticles was studied using a dialysis method. Briefly, lyophilized DOX-NPs (6 mg) were suspended in 3 mL of PBS (0.01 M, pH 7.4), followed by sonication for 10 min to yield an optically clear suspension. The suspensions were introduced into 5 mL-dialyzers (MWCO: 10,000 Da) and immersed in 20 mL of PBS containing Tween 80 (0.1% w/v) at 37° C. in a shaking bath at 100 rpm. At selected time intervals, aliquots (10 mL) were removed from the dissolution medium and an equivalent volume of fresh medium was compensated. The concentration of DOX was immediately measured by UV at 480 nm. The percentage of DOX released was calculated based on a standard curve of known DOX concentrations.

Figure 8A:
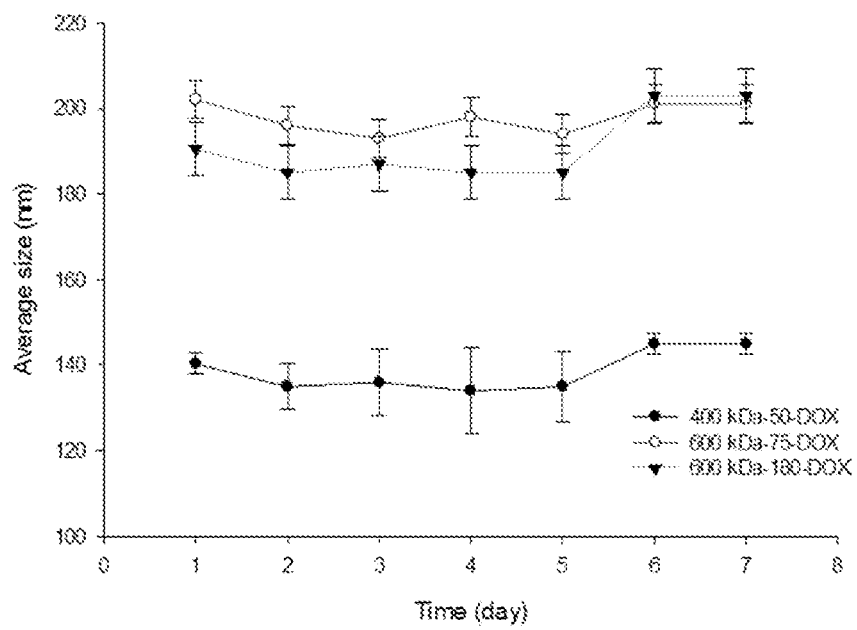
FIG. 8A provides stability of DOX-loaded 400 kDa-50, 600 kDa-75 and 600 kDa-180 nanoparticles in PBS/FBS (1:1) stored at 4° C.

Taking into account that the P(NBCh9-b-NBPEG) nanoparticles are intended for intravenous (i.v.) administration, their stability in a medium containing serum was evaluated. The stability of the DOX-NPs was investigated using DLS to monitor the change in the size of the nanoparticles. The average particle size of DOX-loaded 400 kDa-50, 600 kDa-75, and 600 kDa-180 did not change significantly after 1 week storage at 4° C. in 50% FBS (FIG. 8A), and no precipitation or aggregation was observed.

Figure 8B:
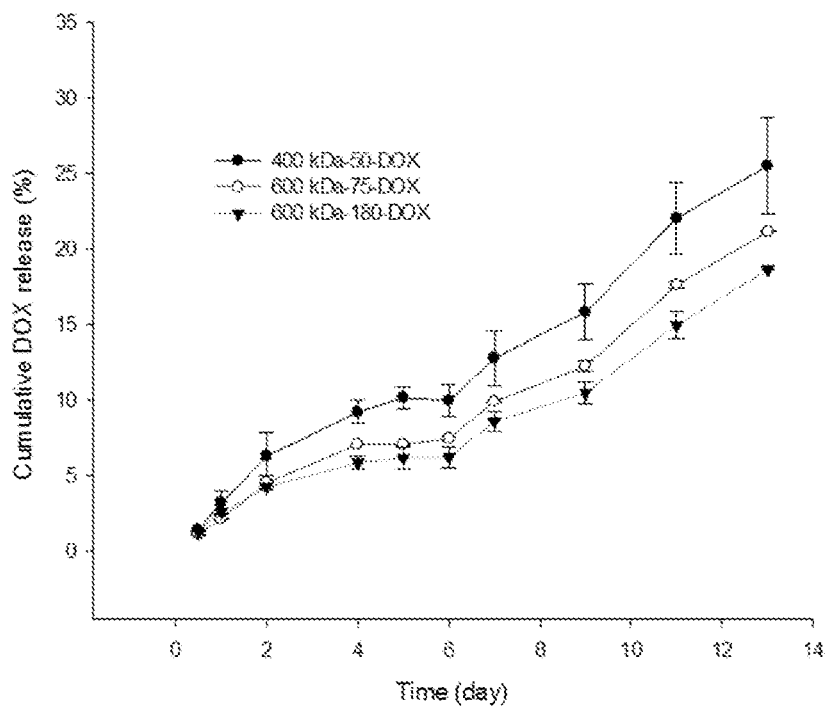
FIG. 8B shows release profiles of DOX-loaded 400 kDa-50, 600 kDa-75, and 600 kDa-180 nanoparticles in PBS (pH 7.4) containing 0.1% Tween 80 at 100 rpm and 37° C.

To further assess the potential of the P(NBCh9-b-NBPEG) nanoparticles as drug carriers, a DOX release test was performed in PBS (pH 7.4, 37° C.) containing 0.1% Tween 80 using a dialysis method. The P(NBCh9-b-NBPEG) nanoparticles released DOX in a sustained release pattern without an initial burst release, with approximately 2% release after the first day, and about 25% for 400 kDa-50-DOX and 17% for 600 kDa-180-DOX nanoparticles after 13 days (FIG. 8B). The drug release from 400 kDa-50 nanoparticles was relatively faster than that from 600 kDa nanoparticles. Despite the significant difference in cholesterol content, DOX release from 600 kDa-75 and 600 kDa-180 was similar. The slow and release properties of the nanoparticles with no burst are useful for delivery of anticancer drugs, in which limited amounts of the drug are released in the blood stream until the nanoparticles reach the tumor tissues where the drug release may be elevated inside cells due to the degradation of the copolymers in the presence of enzymes.

Example 8

Cytotoxicity of DOX-NPs

HeLa cells (7500 cells/well) were seeded on 96-well plates and cultured in 200 μL of DMEM supplemented with 10% FBS, 1% antibiotics, and 1% L-glutamine for 24 h at 37° C. and 5% $CO_2$. After incubation, various concentrations of the blank nanoparticles (0.2-1 mg/mL), DOX-NPs, and free DOX (1-50 μg/mL of DOX equivalents) dissolved in DMEM without supplements were added. After 24 h of incubation with free DOX and DOX-NPs, and 48 h with blank nanoparticles, cytotoxicity was determined using 3-[4,5-dimethylthiazol-2-yl]-3,5-diphenyltetrazolium bromide dye (MTT dye, final concentration of 0.5 mg/mL) uptake at 540 nm on a microplate reader (Tecan group Ltd., Mannedorf, Switzerland).

Figure 9A:
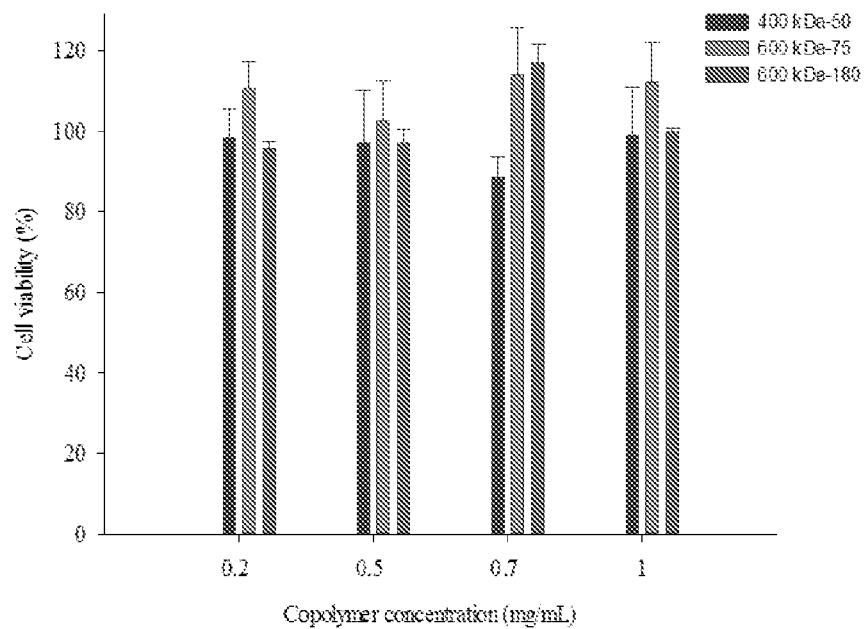
FIG. 9A shows viability of HeLa cells incubated with different concentrations of blank 400 kDa-50, 600 kDa-75, and 600 kDa-180 nanoparticles for 48 h.
Figure 9B:
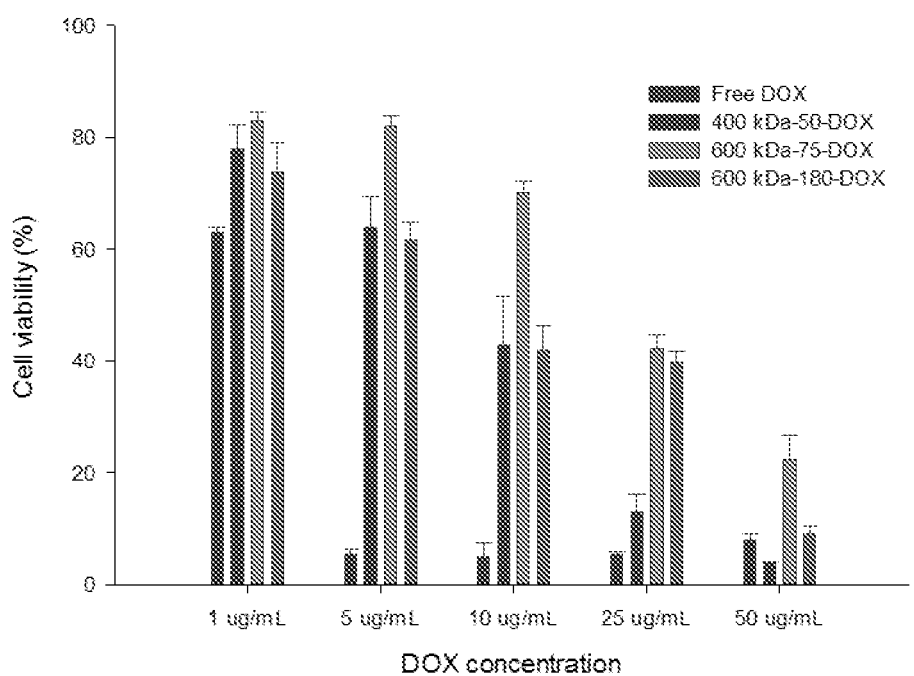
FIG. 9B shows viability of HeLa cells incubated with free DOX, DOX-loaded 400 kDa-50, 600 kDa-75 and 600 kDa-180 nanoparticles at different concentrations of DOX for 24 h.

FIGS. 9A-B show the viability of HeLa cells treated with blank P(NBCh9-b-NBPEG) nanoparticles, free DOX, and DOX-NPs at different nanoparticle and equivalent DOX concentrations. Blank P(NBCh9-b-NBPEG) nanoparticles showed negligible toxicity to HeLa cells even at a concentration of 1 mg/mL with a cell viability of ≥90% 48 h after treatment (FIG. 9A), revealing the low toxicity and good compatibility of the P(NBCh9-b-NBPEG) nanoparticles to the cells. Free DOX and DOX-NPs dose-dependently (1-50 μg/mL DOX) decreased the cell viability by 40-95% after 24 h of incubation (FIG. 9B), suggesting that the P(NBCh9-b-NBPEG) nanoparticles released DOX and delivered to its desired cellular location. By increasing DOX concentration from 1 μg/mL up to 50 μg/mL, free DOX drastically decreased the cell viability while the DOX-NPs gradually decreased the cell viability. At all DOX concentrations, free DOX showed significantly higher cytotoxicity than DOX-NPs. To show a significant cytotoxicity, DOX-NPs taken up by cells must release DOX in the free form. As shown in FIG. 8B, only 3% DOX was released from the nanoparticles within 24 h. As a result, the concentration of DOX released from the nanoparticles was far lower than the concentration of free DOX after specific incubation times. Thus, the difference in the cytotoxicity between free DOX and DOX-NPs was possibly due to the difference in the uptake pathway of free DOX and DOX-NPs, and the sustained-release property of DOX-NPs. At similar DOX levels, the cytotoxicity of DOX-loaded 400 kDa-50 was significantly higher than that of DOX-loaded 600 kDa-75, showing the viability value of about 40% for DOX-loaded 400 kDa-50, and 70% for DOX-loaded 600 kDa-75 at 10 μg/mL DOX. The cytotoxicity of DOX-loaded 400 kDa-50 and DOX-loaded 600 kDa-180 was not significantly different except for 25 μg/mL DOX.

Figure 9C:
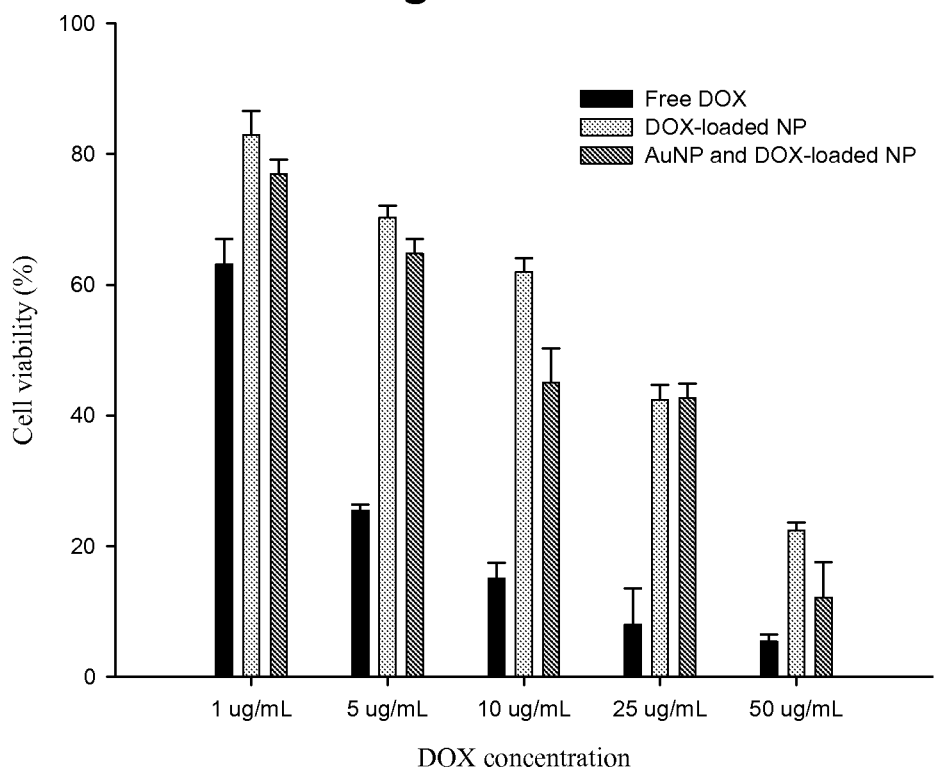
FIG. 9C shows viability of HeLa cells incubated with different concentrations of free Dox, Dox-loaded P(PEOA$_{SH}$-b-PC5A) NPs and Au+DOX-loaded P(PEOA$_{SH}$-b-PC5A) NPs at different concentrations for 24 h.

Similarly, FIG. 9C shows the viability of HeLa cells treated with free DOX, DOX loaded P(PEOASH-b-PC5A) NPs, and Au and DOX loaded P(PEOASH-b-PC5A) NPs.

Example 9

Intracellular Uptake of DOX-NPs

To observe the cellular uptake, HeLa cells were seeded at a density of $1.0×10^5$ cells/well in an 8-well chamber of a Lab-Tek II chamber slide and pre-incubated for 24 h at 37° C. and 5% $CO_2$. Serum-free DMEM containing free DOX and DOX-NPs at equivalent doses (25 µg/mL) was added to each well, followed by incubation for 2 h at 37° C. The cells were then rinsed with PBS, stained with 10 µM Draq5 and fixed with 4% formaldehyde solution for 10 min. Cover glasses were then placed on glass slides. The cellular uptake of free DOX and DOX-NPs was imaged by confocal laser scanning microscopy (Leica, England) at an excitation wavelength of 488 nm for DOX and 633 nm for Draq5.

To quantify cellular uptake, HeLa cells ($5 \times 10^5$ cells/well) in 0.5 mL were grown on a 24-well plate at 37° C. in a humidified atmosphere of 5% $CO_2$ for 24 h. Serum-free DMEM containing free DOX and DOX-NPs at equivalent doses (25 µg/mL) was added to the cells which were subsequently incubated for 2 h. The cells were then washed three times with PBS, harvested by trypsinization and transferred into Fluorescence Activated Cell Sorter (FACS) tubes. All samples were analyzed by flow cytometry (FACSCalibur, BD Biosciences, San Jose, Calif.) to determine cellular internalization. Fluorescence measurements of intracellular DOX were performed in the FL2 channel.

Figure 10:
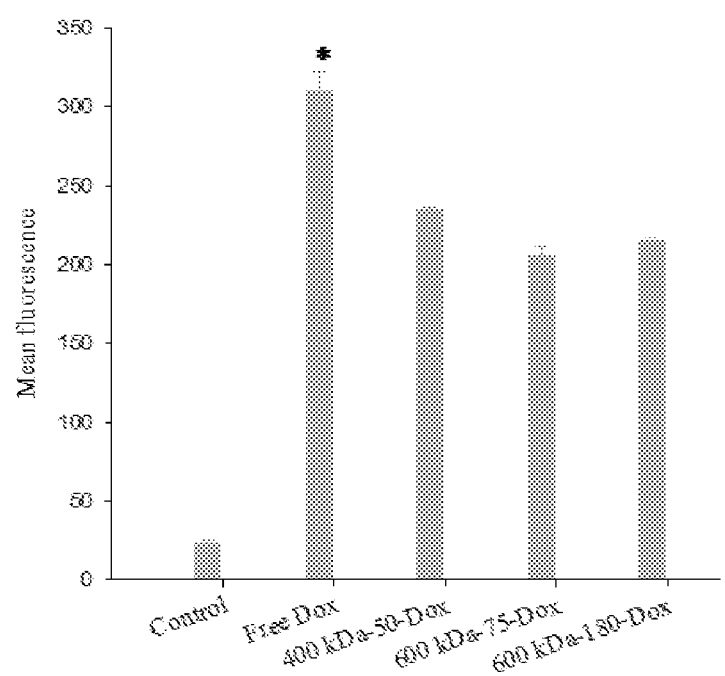
FIG. 10 illustrates mean fluorescence determined by FACS of HeLa cells incubated with free DOX and DOX-loaded 400 kDa-50, 600 kDa-75, and 600 kDa-180 nanoparticles for 2 h at 25 µg/mL DOX equivalence. *P<0.05.

Confocal laser scanning microscopy (CLSM) was employed to investigate the cellular uptake behavior of DOX-NPs in HeLa cells in comparison with that of free DOX. Since DOX itself is fluorescent, it was used directly to investigate cellular uptake without additional markers in the nanoparticles. The nuclei were stained with Draq-5 and changed to a blue color by the confocal software. After 2 h of incubation, free DOX (25 µg/mL)-treated cells presented a strong red color in the nuclei, indicating that free DOX was quickly transported to cytoplasm and diffused to nuclei (results not shown). The intracellular distribution of DOX in the cells incubated with DOX-NPs was significantly different. After 2 h of incubation, intense DOX fluorescence was observed in the cytoplasm rather than in cell nuclei, implying that DOX-NPs could be effectively internalized by HeLa cells. To compare the cellular uptake of free DOX and DOX-NPs, flow cytometry analysis was performed. Because the fluorescence intensity is proportional to the amount of DOX internalized by the cells, the mean fluorescence intensity was used to make a quantitative comparison of cellular uptake (FIG. 10). While the difference in fluorescence intensity of the cells treated with DOX-loaded 400 kDa-50, 600 kDa-75 and 600 kDa-180 nanoparticles was negligible, the cells treated with free DOX showed greater fluorescence intensity than those treated with DOX-NPs at the same equivalent DOX concentration and incubation time. It has been previously reported that the cell membrane is naturally impermeable to complexes with molecular weights larger than 1 kDa. While the molecular weight of DOX is 543.52 Da, the molecular weight of P(NBCh9-b-NBMPEG) nanoparticles is over 400 kDa. Therefore, fast cellular uptake of free DOX molecules was due to the fast diffusion of small molecules through the cell membrane, whereas the cellular uptake of nanoparticles is likely through an endocytosis pathway and they are unable to penetrate the cell nucleus. Due to its fast cellular uptake, the use of free DOX in cancer therapy may cause severe toxicity since it can diffuse rapidly though the body in both healthy and diseased tissue. It is well known that nanoparticles with an ideal size are accumulated within the tumor microenvironment by the EPR effect. The accumulation within tumor tissues, however, may not always correlate with therapeutic outcome since cellular internalization is required for anticancer drugs to exert their biological function inside tumor cells. The results suggest that the efficient cellular uptake of pharmaceutically active molecule-loaded NPs may improve the therapeutic effect of those pharmaceutically active molecules against cancers.

Example 10

In Vivo Circulation Time and Tissue Distribution of DOX-NPs

For in vivo determination of the circulation time, in-house bred Balb/c mice at 6-8 weeks old were randomly divided into two groups of 5 mice per group and were injected intravenously with free DOX and DOX-NPs at a single dose of 5 mg/kg of equivalent DOX. At 5 min, 15 min, 30 min, 1 h, 2 h, 4 h, 6 h, 8 h, 24 h post injection, blood (150 µL) was collected via facial vein into heparinized tubes for two time points and then mice were sacrificed for blood collection of next time point by cardiac puncture. Each group of mice had three time points for blood collection. Plasma was separated by centrifugation (3000 rpm, 10 min, 4° C.) and stored at −80° C. until analyzed.

For the tissue distribution study, tumor-bearing severe combined immunodeficient (SCID) between 6 and 8 weeks-old mice were inoculated with 0.1 mL PBS containing $2 \times 10^6$ human lung cancer cells (A549) into the right flank. Four weeks after tumor implantation, free DOX and DOX-NPs (100 µL) at 2.5 mg/kg of equivalent DOX were injected into the tail-vein. Twenty four hours after injection, mice were sacrificed for blood and organ collection including tumor, liver, spleen, kidney, lung, and heart. Tissues were then weighed and homogenized in the lysis buffer (0.1 M Tris-HCl, 2 mM EDTA, 0.1% Triton X-100) using a probe sonicator (Qsonica LLC, CT). The lysate of each tissue was centrifuged at 14,000 rpm for 20 min at 4° C. The blood was centrifuged at 3000 rpm for 10 min at 4° C.

Sample extraction was performed using a reported procedure with some modifications. Briefly, plasma (50 µL) or tissue (100 µL) was spiked with 100 µL of idarubicin (1 µg/mL) as an internal standard (IS). After adding 100 µL of 1.0 M Tris buffer solution, the extraction of DOX and IS was performed twice by adding 2.5 mL of a choloroform/methanol (75:25, v/v) mixture and vortexing for 5 min. After centrifugation at 8000 rpm for 10 min, the samples in the organic phase were collected evaporated to dryness under a flow of nitrogen at ambient temperature. Dry residues from plasma and tissues were dissolved in 100 µL methanol followed by centrifugation to remove any precipitate. The resulting supernatant was analyzed using an HPLC apparatus equipped with an autosampler and a fluorescence detector (Shimadzu, Kyoto, Japan). A 20-µl sample was injected onto a $C_{18}$ column (Kinetex 5 µm, 150×4.6 mm, Phenomenex, Calif.) using a mixture of 0.05 M sodium acetate (pH 4.0) and acetonitrile (73.5:26.5) as the mobile phase. The flow rate was 1 mL/min and the signals were monitored by fluorescence detection at excitation and emission wavelength (Ex/Em) of 480/558 nm.

Figure 11A:
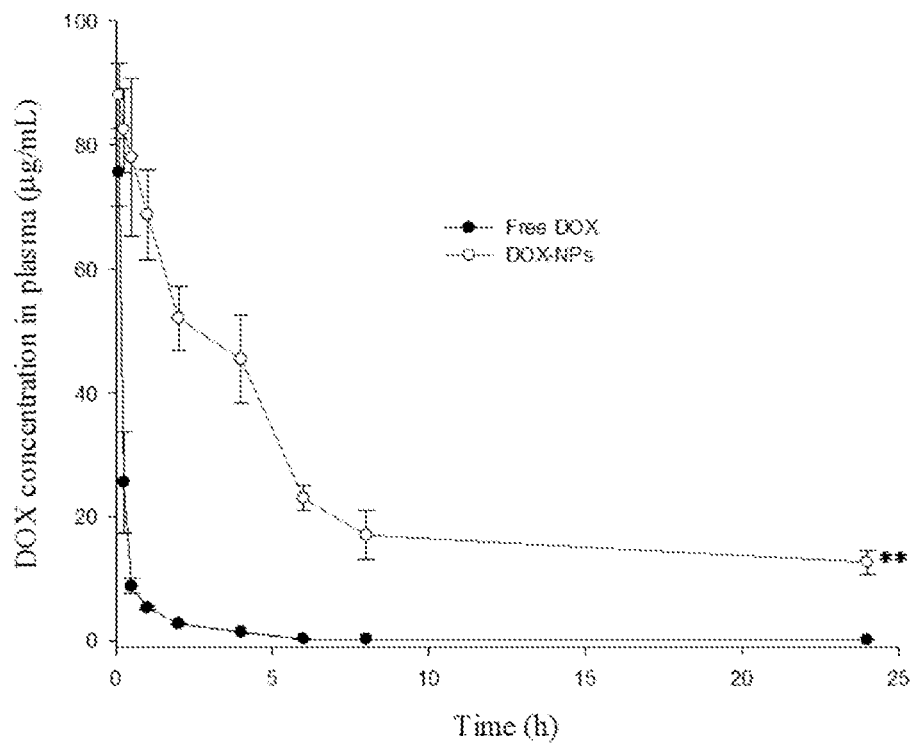
FIG. 11A provides in vivo circulation time of free DOX and DOX-NPs.

FIG. 11A shows plasma concentration-time profiles of DOX after i.v injection of free DOX and DOX-NPs at a dose of 5 mg/kg. Plasma concentration of free DOX was 75.6±5 µg/mL at 5 min post-injection but dramatically decreased to 5.3±0.3 µg/mL 1 h after injection and to 1.4±0.1 µg/mL 4 h after injection, indicating rapid elimination of free DOX from the circulation. In contrast, DOX-NPs displayed markedly delayed blood clearance, showing plasma concentration of DOX of 88.0±5.2 µg/mL at 5 min post-injection, 68.8±7.3 µg/mL at 1 h and 45.4±7.1 µg/mL at 4 h post-injection. Notably, 24 hours after administration of the DOX-NPs, the DOX plasma concentration was still 12.6±1.9 μg/mL, whereas it was almost undetectable for the free DOX at this time point. As a result of the rapid clearance of free DOX, the drug found in the serum is believed to be encapsulated in the nanoparticles. Such increased circulation time may be attributed to DOX molecules being stabilized within the core of the P(NBCh9-b-NBPEG) nanoparticles, preventing their renal clearance and metabolism by enzymes in the liver. Such behavior of the P(NBCh9-b-NBPEG) nanoparticles induced by their nanosize and the hydrophilic PEG shell may decrease the rate of mononuclear phagocyte system (MPS) uptake and reduce plasma protein absorption. A successful passive drug targeting to tumor tissue is based on long circulation times of nanoparticles within the blood stream to exploit the EPR effect, and the stability of drug encapsulation in the nanoparticle core. Thus, the pharmaceutically active molecule-loaded NPs with stability and long circulation times are likely to preferentially accumulate in tumor tissues.

Figure 11B:
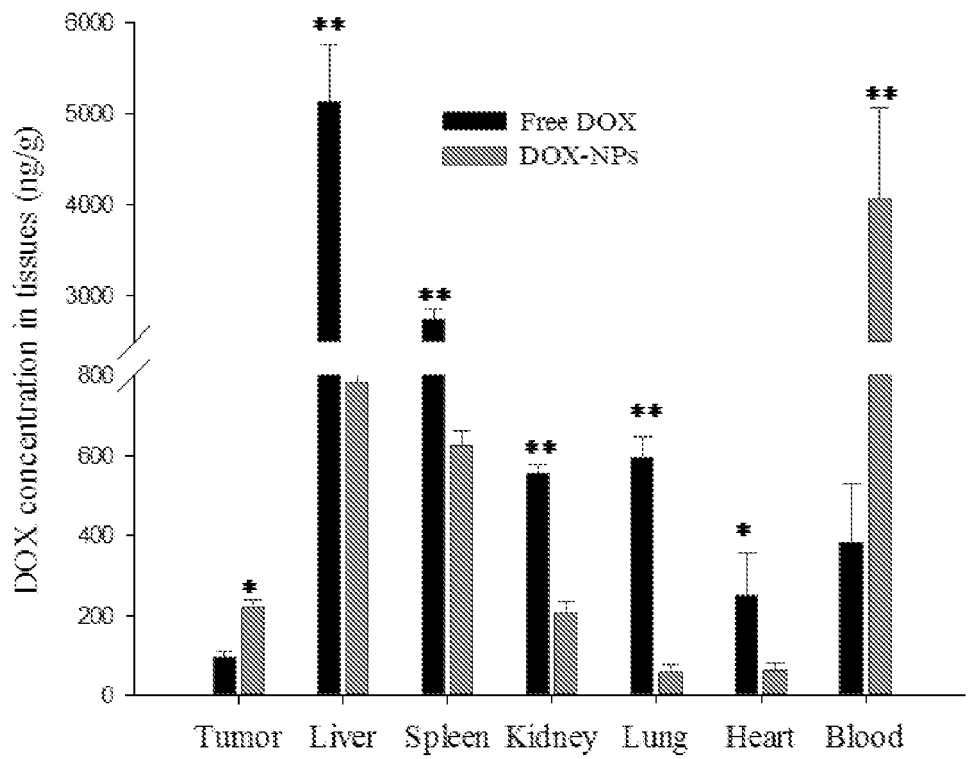
FIG. 11B shows tissue distribution of DOX and DOX-NPs in tumor-bearing SCID mice after 24 h injection. Data are presented as mean±SD (n=5) *P<0.05, **P<0.01.

As seen in FIG. 11B, the concentration of DOX following administration of free DOX was greatest in the liver and lowest in the tumor. In contrast, the concentration of DOX after administration of DOX-NPs was greatest in blood, and the tumor concentration was significantly greater than observed following administration of free DOX. The results suggested that while free DOX was widely distributed in the body, it was mainly captured in the host defense and metabolic organs such as liver, spleen, lung, and kidney and metabolized or rapid excreted by these organs leading to low drug concentration in tumor. Notably, the 6.5-fold lower concentration in liver and 2.3-fold higher concentration in tumor of DOX were achieved 24 h after administration of DOX-NPs compared to that of free DOX. The DOX plasma level following administration of DOX-NPs was 11-fold greater than after free DOX administration at the same dose. This high drug concentration in plasma may contribute to further accumulation of the DOX-NPs in tumor tissue with increasing blood circulation time of the nanoparticles. Furthermore, the DOX-NPs decreased the drug concentration in the heart by 3.9-fold compared with free drug. Thus, the P(NBCh9-b-NBPEG) nanoparticles may significantly reduce the cardiotoxicity of DOX since cardiomyopathy is the dose-limiting side effect of free DOX. Meanwhile, the nanoparticles also decreased the DOX level in the lungs by 10 fold compared with free DOX, which might depress the damage to the lung and increase its biosafety. The results confirmed that DOX-NPs with its PEG shielding effect and excellent stability exhibited longer blood circulation, less uptake by the MPS and higher tumor accumulation than the free drug.

Example 11

In Vivo Imaging of the P(NBCh9-b-NBPEG) Nanoparticles

The biodistribution of P(NBCh9-b-NBPEG) self-assembled nanoparticles was assessed by in-vivo near-infrared (NIR) imaging. A NIR fluorophore, DiR, was loaded into the nanoparticles by a dialysis method as described in Section 2.5. Briefly, the P(NBCh9-b-NBPEG) (10 mg) and DiR (0.6 mg) were dissolved in DMF (3 mL). The resulting solution was dialyzed against distilled water for 48 h, and then filtered through a 0.45 μm membrane before lyophilization. The loading content of DiR was determined spectrophotometrically at a wavelength of 750 nm.

The tumor models were established by subcutaneous injection of A549 cells ($2\times10^6$ cells in 100 μL of PBS) into the flank of male SCID mice. When the tumor reached an acceptable size, the mice were treated with the DiR-loaded self-assembled nanoparticles (5 μg/kg of equivalent DiR) via tail-vein injection. Whole body images were obtained at 1, 5, and 24 h after injection using the Maestro in vivo imaging system (Cambridge Research & Instrumentation, Inc., Woburn, Mass.). Images of various organs, including heart, kidney, liver, spleen, lung, and tumor, were also obtained after sacrifice of the mice 24 h after injection.

Figure 12A:
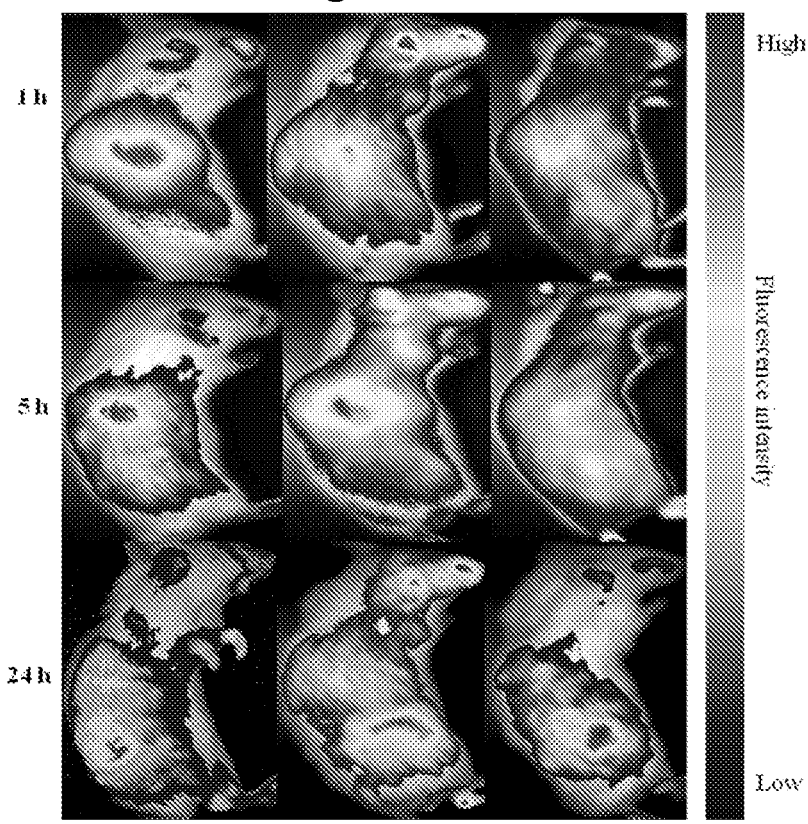
FIG. 12A provides in vivo fluorescence images of DiR-loaded nanoparticles in tumor-bearing SCID mice at 1 h, 5 h, 24 h-post injection.
Figure 12B:
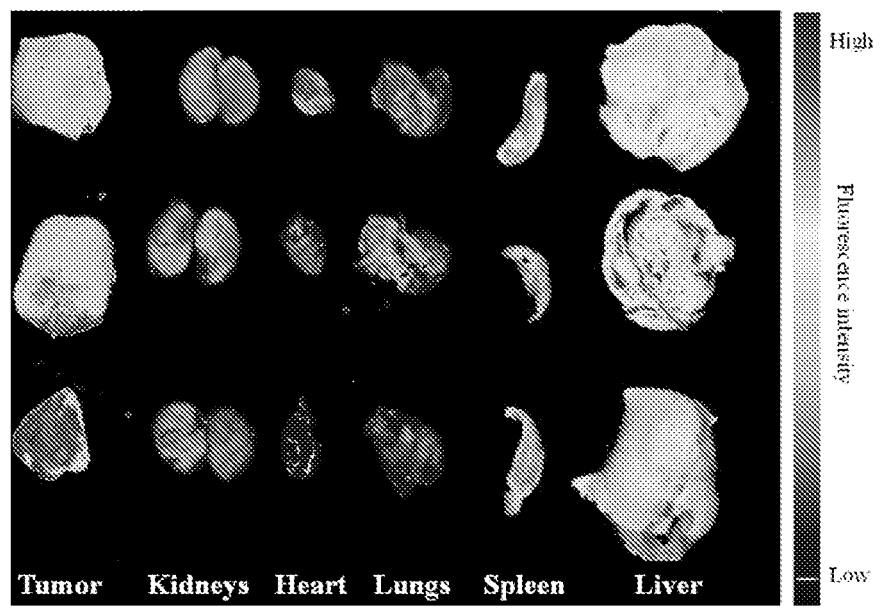
FIG. 12B shows ex vivo fluorescence images of organs and tumors in SCID mice after 24 h injection.

At 1 h post-injection, fluorescence could be detected throughout the entire animal, and a strong fluorescent signal was visualized in the liver, indicating that the nanoparticles accumulated primarily in the liver (FIG. 12A). The intense whole-body fluorescence was continuously observed at 5 h post-injection, indicating the long circulation time of the DiR-loaded P(NBCh9-b-NBPEG) nanoparticles. Moreover, the contrast of the DiR signal in the tumor compared to the surrounding tissues of the animal was already apparent 5 h post-injection of the P(NBCh9-b-NBPEG) nanoparticles. After 24 h, a strong red signal was observed in tumor tissues and only a low signal was observed in the liver. At 24 h post-injection, the mice were sacrificed and the major organs were isolated to analyze the tissue distribution of the DiR-loaded nanoparticles. As shown in FIG. 12B, the highest NIRF intensity was observed in tumor tissues, while the signal intensities were lower for other tissues, with a particularly low fluorescence signal in the heart. The results indicated the effective accumulation of the P(NBCh9-b-NBPEG) nanoparticles in tumor tissue. Without being bound to a particular theory, it is believed that this appreciable tumor specific delivery of P(NBCh9-b-NBPEG) nanoparticles may have resulted from the prolonged circulation time achieved by the stability of the nanoparticles and the EPR effect in tumor tissue due to their small size.

Example 12

Evaluation of Antitumor Activity

The antitumor efficacy of DOX and DOX-NPs was evaluated in SCID mice inoculated subcutaneously in the right flank with 0.1 mL PBS containing $2\times10^6$ A549 cells. When the tumors grew to approximately 20-30 mm³ (9 days after tumor implantation), the mice were randomly divided into three groups (n=5-6), and this day was designated as day 0. The mice were injected intravenously twice a week via tail vein with saline (control), free DOX and DOX-NPs (100 μL) at 2.5 mg/kg of equivalent DOX. Antitumor activity was evaluated in terms of tumor volume which was calculated using the following equation: Tumor volume (mm³)= width²×length/2. The body weight was measured simultaneously as an indicator of the systemic toxicity.

Figure 13:
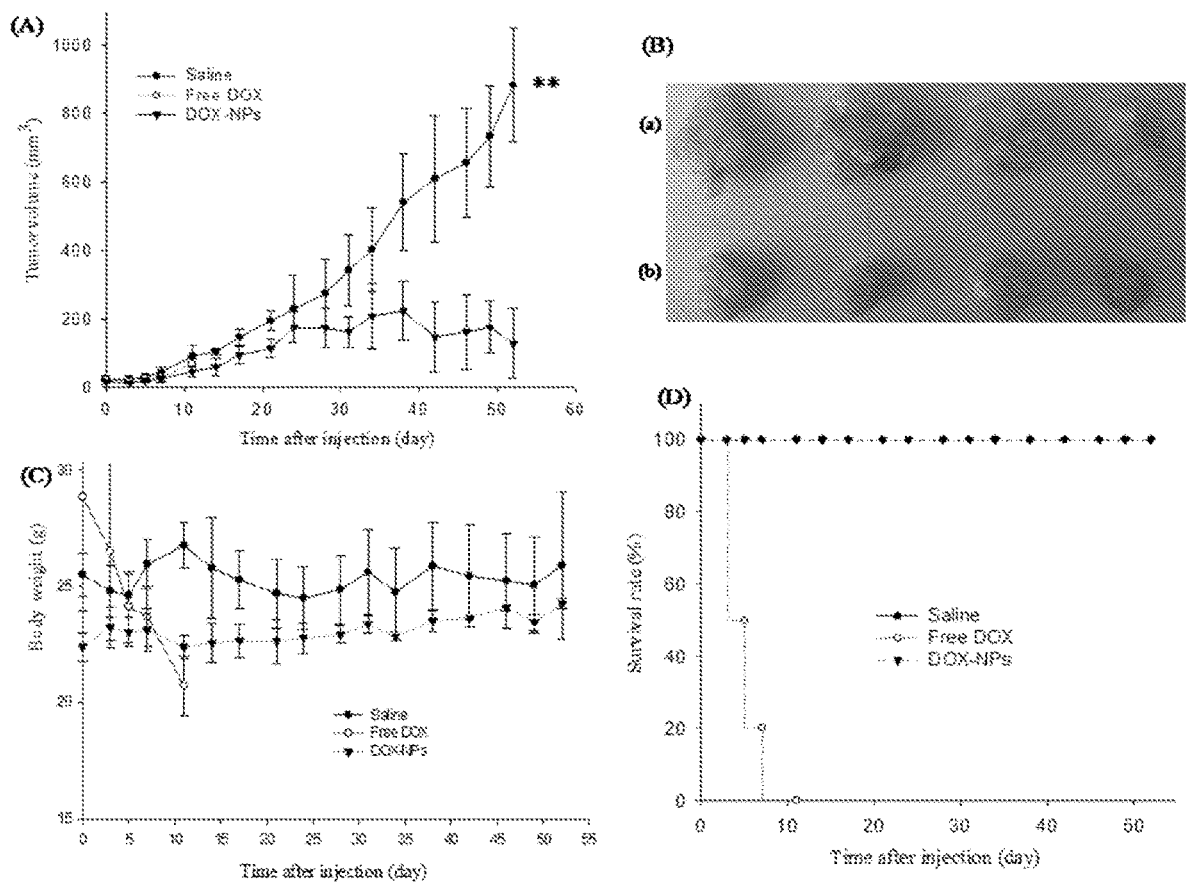
FIG. 13 shows antitumor efficacy of DOX-NPs in tumor-bearing SCID mice: (A) tumor volume, (B) photo of tumor tissue at the end of the study (a) control, (b) mice treated with DOX-NPs, (C) body weight change, and (D) survival rate. Data are presented as mean±SD (n=5), **P<0.01.

FIG. 13 shows the changes in tumor volume, body weights, and survival rates of the mice treated with free DOX and DOX-NPs at 2.5 mg/kg DOX. The tumor volumes in the control group (saline) and the group treated with DOX-NPs slowly increased to about 230.7±98.2 mm³ and 176.6±44.0 mm³ within 24 days, respectively (FIG. 13A). Although tumor growth was inhibited by free DOX treatment, the body weight of this group of animals dramatically decreased compared to the control and DOX-NPs treated groups (FIG. 13C), suggesting that severe toxicity was induced by free DOX at the given dose. Eventually, all the animals in the DOX group on day 11 had to be terminated for humanitarian reasons. After 24 days, the tumor volume of the control group rapidly increased and reached 883.4±165.7 mm³ at day 52. In contrast, the tumor volume of the group treated with DOX-NPs slightly increased to 224.8±84.7 mm³ and began to decrease after 38 day injection, and was further reduced to 130±102.0 mm³ at day 52, indicating that the treatment group had significantly lower mean tumor volume (p<0.01) than the control group. In addition, compared to the initial tumor volume (approximately 30 mm³), the tumor volume barely increased in the DOX-NPs treated mice, indicating that DOX-NPs effectively suppressed tumor growth. All mice were sacrificed and tumors were excised after 52 days of treatment. FIG. 13B shows the representative photographs of each group at the end of the experiment. The tumor size of the control group was larger than that of the treatment groups, which was consistent with the results of the relative tumor volume measurements. The enhanced in vivo efficacy can be explained by the enhanced accumulation of the DOX-NPs at the tumor site due to their effective maintenance of DOX within the core, thus preventing their leakage in the blood stream during the prolonged blood circulation. In addition, once DOX-NPs had accumulated in tumor tissue, the sustained release of DOX from the nanoparticles increased the exposal time of DOX to tumor cells, resulting in the suppression of tumor growth.

Body weight change is an important indicator of drug related toxicity in tumor-bearing animals. As shown in FIGS. 13C-D, treatment of the tumor-bearing SCID mice with free DOX at 2.5 mg/kg resulted in rapid decrease in body weight (28.1±1.2%) and the death of all mice within 11 days after the third injection, demonstrating that the free drug was toxic in the tumor-bearing SCID mice. The treatment with DOX-NPs appeared to be well-tolerated and had almost no decrease in body weight and no change in the survival rate compared to the control group. These results demonstrated enhanced antitumor activity and greatly reduced toxicity of DOX when incorporated into the P(NBCh9-b-NBPEG) nanoparticles.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:

1. A block copolymer comprising:
a first block, which is of formula:

and a second block, which is of formula:

wherein
m and n are independently an integer about 3 to about 500;

A is independently selected from polynorbonene, polycyclopentene, polycyclooctene, polyacrylate, polymethacrylate, and a polysiloxane;

$R_1$ is a steroid moiety optionally comprising a linker; and $R_2$ is a polyalkylene oxide moiety.

2. The block copolymer of claim 1, wherein the steroid moiety comprises cholesterol, cholic acid, deoxycholic acid, or taurocholic acid.

3. The block copolymer of claim 2, wherein the steroid moiety comprises cholesterol.

4. The block copolymer of claim 1, wherein the linker at $R_1$ is

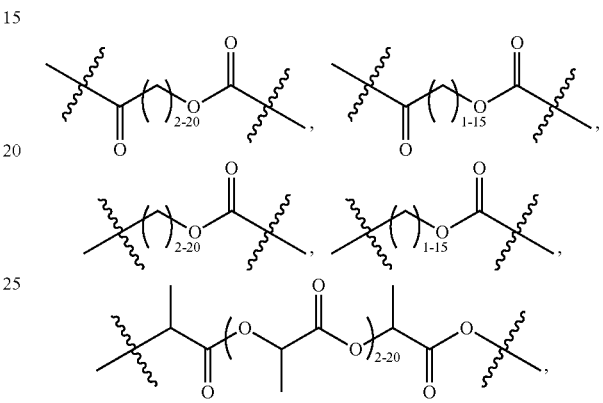

a polylactone, or an oligomer of siloxane.

5. The block copolymer of claim 1, wherein the polyalkylene oxide moiety comprises polyethylene oxide or polyethylene oxide thiolate.

6. The block copolymer of claim 1, wherein each A is independently polynorbonene or polyacrylate.

7. The block copolymer of claim 1, comprising the structure:

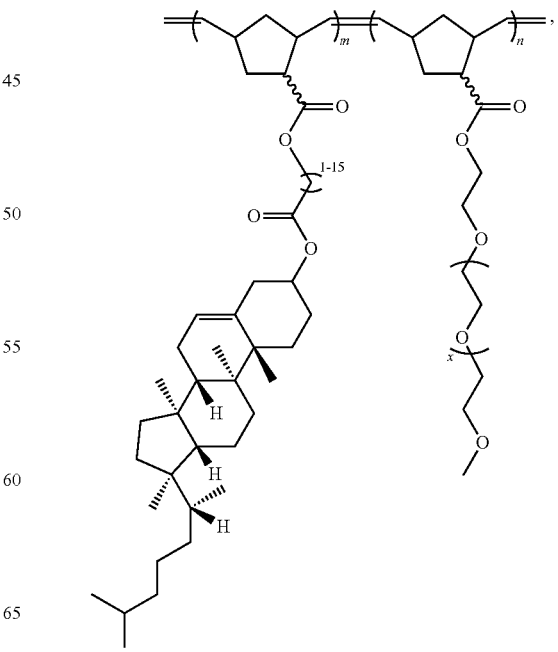

35
-continued
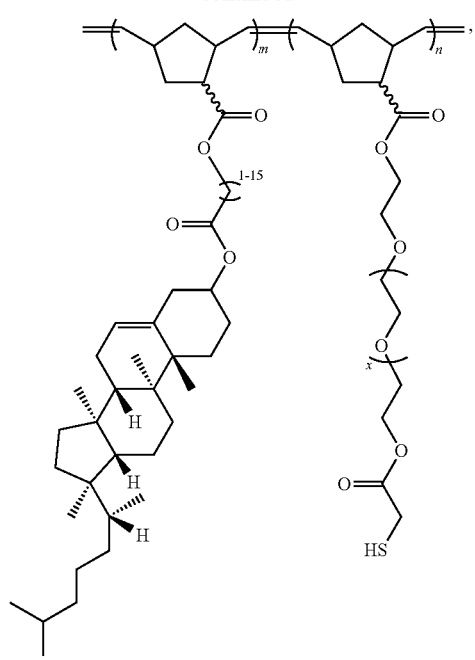
36
-continued
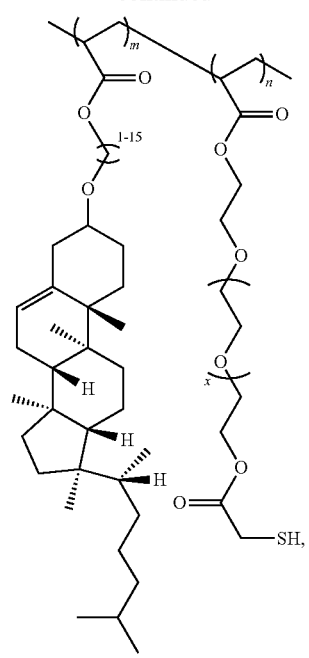
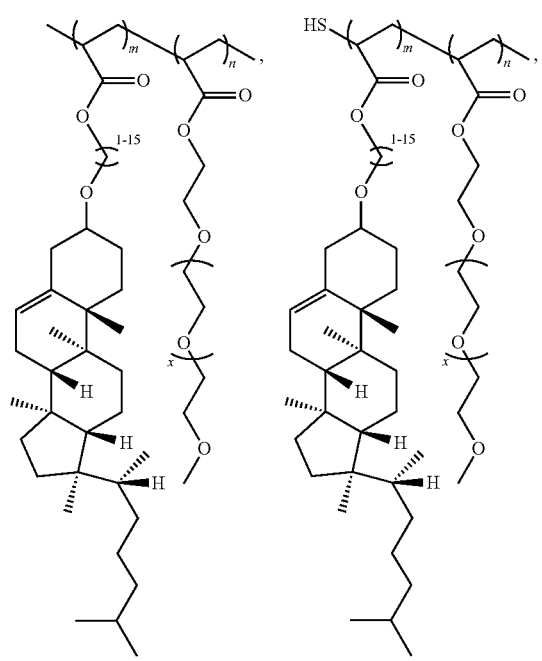
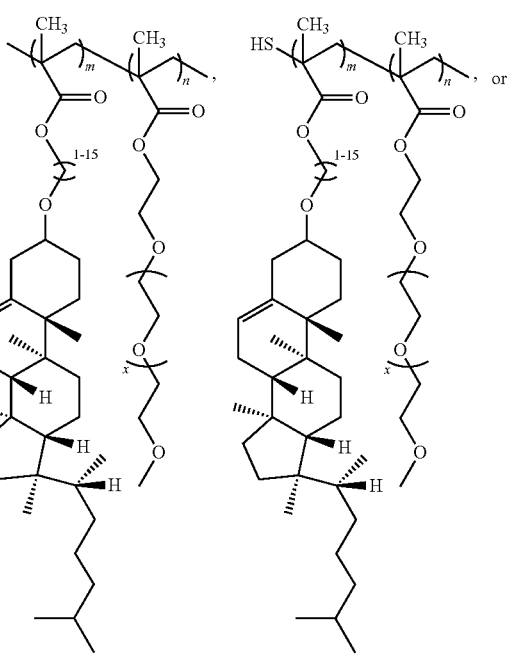

-continued

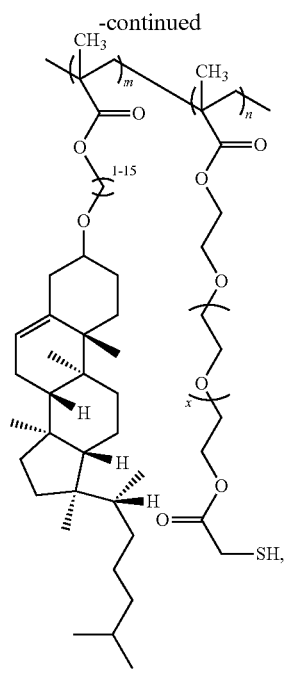

wherein
x is an integer between about 3 and about 100;
m is an integer between about 5 and about 200; and
n is an integer between about 5 and about 100.

8. The block copolymer of claim 7, wherein x is between about 5 and about 50.

9. The block copolymer of claim 7, wherein m is between about 10 and about 100.

10. The block copolymer of claim 7, wherein n is between about 15 and about 85.

11. The block copolymer of claim 1, wherein the molecular weight of the block copolymer is about 10,000 to about 1,000,000 Da.

12. The block copolymer of claim 1, wherein the block copolymer is in a core/shell nanoparticle form.

13. A nanoparticle comprising a block copolymer nanoparticle in a core/shell form and a hydrophobic pharmaceutically active molecule, wherein the block polymer comprises:
a first block, which is of formula:

and a second block, which is of formula:

wherein
m and n are independently an integer about 3 to about 500;
A is independently selected from polynorbonene, polycyclopentene, polycyclooctene, polyacrylate, polymethacrylate, and a polysiloxane;
$R_1$ is a steroid moiety optionally comprising a linker; and
$R_2$ is a polyalkylene oxide moiety.

14. The nanoparticle of claim 13, wherein the hydrophobic molecule is doxorubicin, daunorubicin, vincristin, paclitaxel, docetaxel, cisplatin, camptothecin, irinotecan, 5-fluorouracil, methotrexate, or dexamethasone.

15. The nanoparticle of claim 13, further comprising one or more metal nanoparticles.

16. The nanoparticle of claim 15, wherein the metal nanoparticle is a gold nanoparticle, a magnetic nanoparticle, or a quantum dot.

17. The nanoparticle of claim 13, wherein the nanoparticle is between about 5 and about 500 nm in diameter.

18. A method of delivering a pharmaceutically active molecule, comprising administering to a subject the nanoparticle according to claim 13.

19. A process for preparing a nanoparticle of claim 13, comprising
(a) dissolving a block copolymer in an organic solvent to obtain a copolymer solution,
wherein the block polymer comprises
a first block, which is of formula:

and a second block, which is of formula:

wherein
m and n are independently an integer about 3 to about 500;
A is independently selected from polynorbonene, polycyclopentene, polycyclooctene, polyacrylate, polymethacrylate, and a polysiloxane;
$R_1$ is a steroid moiety optionally comprising a linker; and
$R_2$ is a polyalkylene oxide moiety; and
(b) mixing the copolymer solution in an aqueous solution to form a nanoparticle.

20. The nanoparticle of claim 13, wherein the steroid moiety comprises cholesterol, cholic acid, deoxycholic acid, or taurocholic acid.

21. The nanoparticle of claim 13, wherein the linker at $R_1$ is

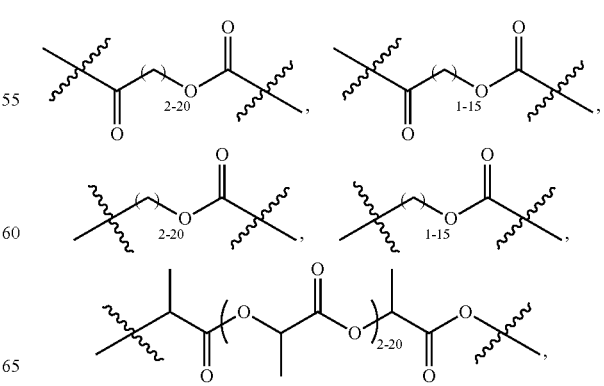

a polylactone, or an oligomer of siloxane.

22. The nanoparticle of claim 13, wherein the polyalkylene oxide moiety comprises polyethylene oxide or polyethylene oxide thiolate.
23. The nanoparticle of claim 13, wherein each A is independently polynorbonene or polyacrylate.
24. The nanoparticle of claim 13, comprising the structure:
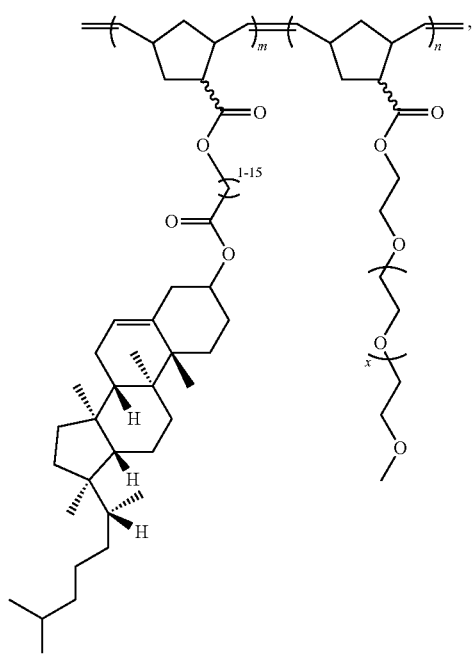
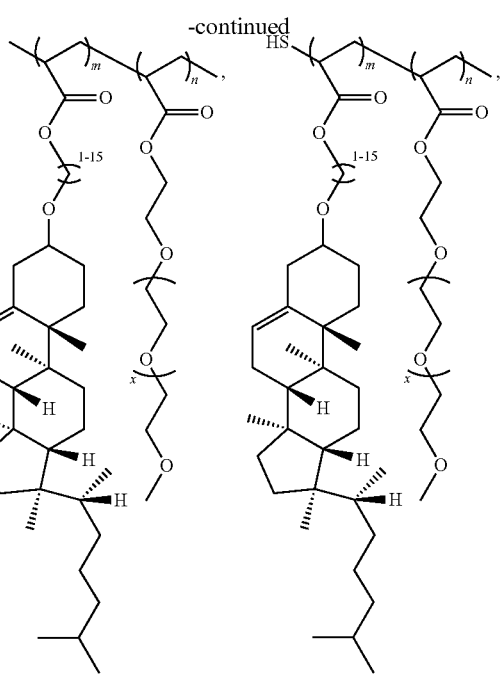
-continued
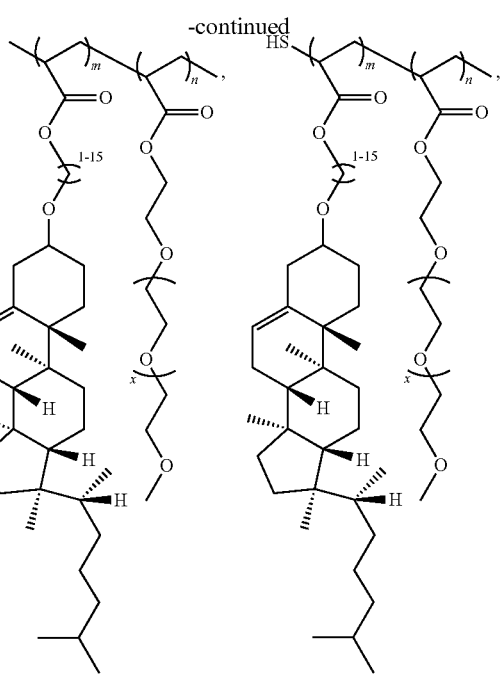
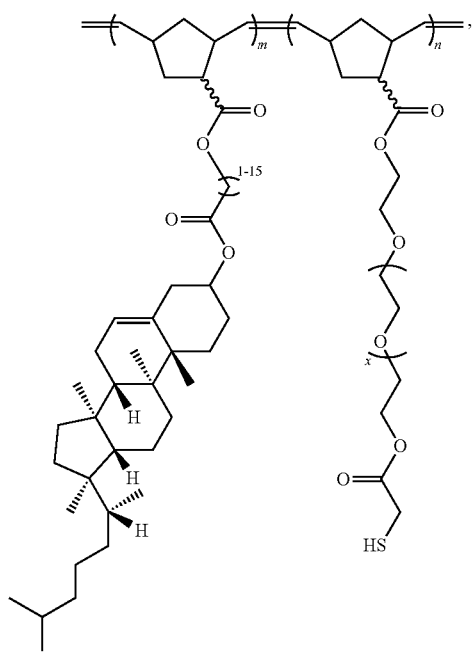
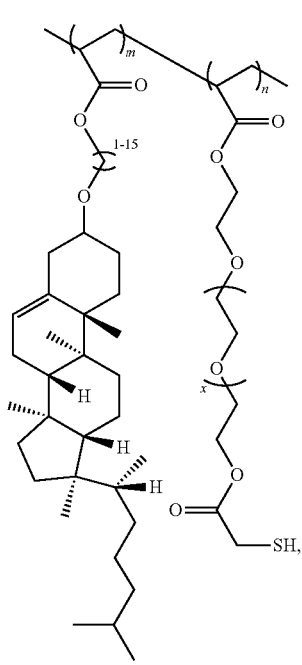

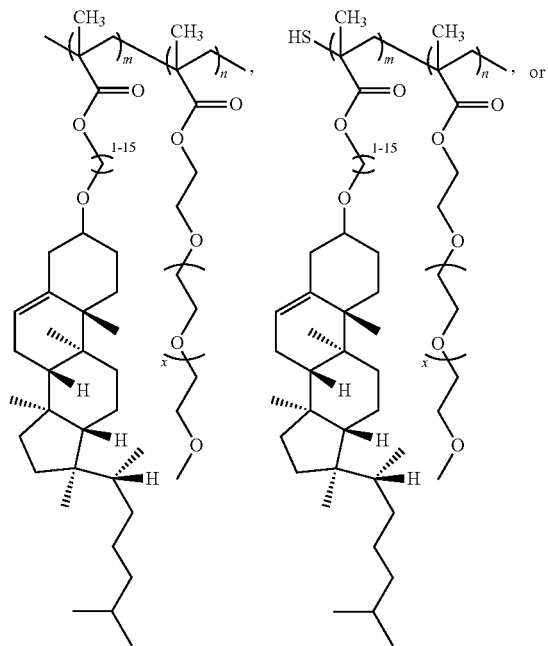
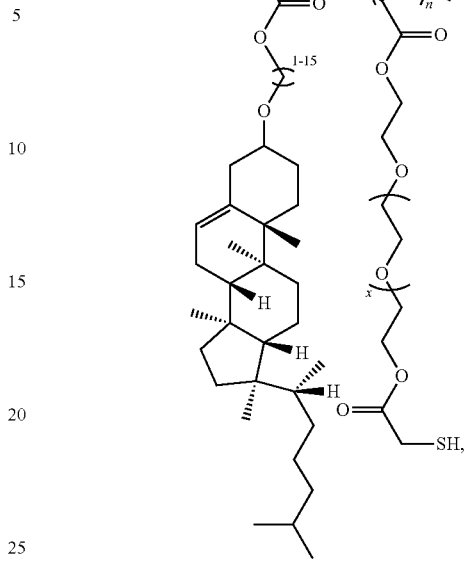
wherein
x is an integer between about 3 and about 100;
m is an integer between about 5 and about 200; and
n is an integer between about 5 and about 100.
25. The nanoparticle of claim 13, wherein x is between about 5 and about 50; m is between about 10 and about 100; and n is between about 15 and about 85.
26. The nanoparticle of claim 13, wherein the molecular weight of the block copolymer is about 10,000 to about 1,000,000 Da.
* * * * *